(12) United States Patent
Ellis et al.

(10) Patent No.: US 10,920,239 B2
(45) Date of Patent: Feb. 16, 2021

(54) MAIZE EVENT MON87429 AND METHODS OF USE THEREOF

(71) Applicant: Monsanto Technology LLC, St. Louis, MO (US)

(72) Inventors: Christine M. Ellis, Manchester, MO (US); Michael E. Goley, St. Charles, MO (US); Jintai Huang, Chesterfield, MO (US); Tracy E. Klingaman, St. Charles, MO (US); Clayton T. Larue, Chesterfield, MO (US); Youlin Qi, Chesterfield, MO (US); Oscar C. Sparks, Florissant, MO (US); Brook M. Van Scoyoc, O'Fallon, MO (US); Heping Yang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 31 days.

(21) Appl. No.: 16/259,985

(22) Filed: Jan. 28, 2019

(65) Prior Publication Data

US 2019/0241903 A1 Aug. 8, 2019

Related U.S. Application Data

(60) Provisional application No. 62/625,537, filed on Feb. 2, 2018.

(51) Int. Cl.
*C12N 15/82* (2006.01)
*C12Q 1/68* (2018.01)
(Continued)

(52) U.S. Cl.
CPC ..... *C12N 15/8274* (2013.01); *C12N 15/8223* (2013.01); *C12N 15/8275* (2013.01);
(Continued)

(58) Field of Classification Search
None
See application file for complete search history.

(56) References Cited

U.S. PATENT DOCUMENTS

| 8,501,407 B2 | 8/2013 | Brinker et al. | |
| 8,618,358 B2 * | 12/2013 | Feng | A01H 1/02 800/300 |

(Continued)

OTHER PUBLICATIONS

International Search Report and Written Opinion regarding PCT Application No. PCT/US2019/015429, dated May 6, 2019, 11 pages.

(Continued)

*Primary Examiner* — Ashley K Buran
(74) *Attorney, Agent, or Firm* — Dentons US LLP; Lawrence Lavin

(57) ABSTRACT

The invention provides recombinant DNA molecules that are unique to maize event MON87429 and transgenic maize plants, maize plant parts, maize seeds, maize cells, and agricultural products containing maize event MON87429 as well as methods of using and detecting maize event MON87429. Transgenic maize plants containing maize event MON87429 exhibit tolerance to inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS).

19 Claims, 3 Drawing Sheets

Specification includes a Sequence Listing.

(51) Int. Cl.
*C12Q 1/6876* (2018.01)
*C12Q 1/686* (2018.01)
*C12Q 1/6874* (2018.01)
*C12Q 1/6895* (2018.01)

(52) U.S. Cl.
CPC ......... *C12N 15/8277* (2013.01); *C12Q 1/686* (2013.01); *C12Q 1/6874* (2013.01); *C12Q 1/6876* (2013.01); *C12Q 1/6895* (2013.01); *C12Q 2600/13* (2013.01)

(56) References Cited

U.S. PATENT DOCUMENTS

| | | |
|---|---|---|
| 8,735,661 B2 | 5/2014 | Brinker et al. |
| 9,024,115 B2 | 5/2015 | Brinker et al. |
| 9,139,838 B2 | 9/2015 | Huang et al. |
| 9,447,428 B2 | 9/2016 | Brinker et al. |
| RE46,292 E | 1/2017 | Brinker et al. |
| 9,816,106 B2 | 11/2017 | Huang et al. |
| 10,023,874 B2 | 7/2018 | Ellis et al. |
| 10,030,277 B2 | 7/2018 | Brinker et al. |
| 10,113,178 B2 | 10/2018 | Burns et al. |
| 2010/0080887 A1 | 4/2010 | Wagner et al. |
| 2012/0246763 A1 | 9/2012 | Flasinski |
| 2013/0031672 A1 | 1/2013 | Flasinski et al. |
| 2014/0109250 A1 | 4/2014 | Feng et al. |
| 2016/0319299 A1 | 11/2016 | Brinker et al. |
| 2017/0029841 A1 | 2/2017 | Huang et al. |
| 2018/0030474 A1 | 2/2018 | Huang et al. |
| 2018/0363068 A1 | 12/2018 | Brinker et al. |
| 2019/0017066 A1 | 1/2019 | Ellis et al. |
| 2019/0055575 A1 | 2/2019 | Burns et al. |
| 2019/0300898 A1 | 10/2019 | Brinker et al. |

OTHER PUBLICATIONS

Mathieu et al., "Export of FT Protein from Phloem Companion Cells is Sufficient for Floral Induction in Arabidopsis," Current Biology, 17: 1055-1060; Jun. 19, 2007.
GenBank Accession No. AC187137, dated Sep. 24, 2013.
GenBank Accession No. EZ935721, dated Feb. 4, 2011.
U.S. Appl. No. 16/737,870, filed Jan. 8, 2020, Feng, et al.
Formal Reply to Written Opinion regarding PCT Application No. PCT/US2019/015429, filed Nov. 25, 2019, 10 pages.
U.S. Appl. No. 16/844,949, filed Apr. 9, 2020, Huang et al.

* cited by examiner

MAIZE EVENT MON87429 AND METHODS OF USE THEREOF

CROSS-REFERENCE TO RELATED APPLICATIONS

This application claims the benefit of priority of U.S. Provisional Application No. 62/625,537, filed Feb. 2, 2018, the disclosure of which is hereby incorporated by reference in its entirety.

INCORPORATION OF SEQUENCE LISTING

The sequence listing that is contained in the file named "MONS430US-seq.txt", which is 44.2 KB (measured in MS-Windows) and created on Jan. 17, 2019, is filed herewith by electronic submission and incorporated herein by reference.

FIELD OF THE INVENTION

The invention relates to recombinant DNA molecules of maize event MON87429. The invention also relates to transgenic maize plants, parts, seeds, cells, and agricultural products containing the maize event MON87429 as well as methods of using transgenic maize plants, parts, seeds, cells, and agricultural products containing the maize event MON87429 and detecting maize event MON87429. Transgenic maize plants, parts, seeds, and cells containing maize event MON87429 exhibit tolerance to inhibitors of acetyl CoA carboxylase (ACCase) in the aryloxyphenoxy propionate (FOP) group such as quizalofop and haloxyfop; synthetic auxins such as dicamba and 2,4-D; inhibitors of glutamine synthetase such as glufosinate; and inhibitors of 5-enolpyruvylshikimate-3-phosphate synthase (EPSPS) such as glyphosate.

BACKGROUND OF THE INVENTION

Maize (*Zea mays*) is an important crop in many areas of the world, and the use of herbicides for weed control in crop production is a well-established tool. The methods of biotechnology have been used to produce transgenic maize that are tolerant to a specific herbicide due to the expression of a heterologous gene, also known as a transgene. An herbicide tolerance trait can be used alone or combined with other traits, such as tolerance to another herbicide or resistance to pests or pathogens. Combinations of herbicide tolerance traits are desirable to provide weed control options that increase grower flexibility and enable the use of multiple herbicide mode of actions for controlling challenging weeds. A combination of traits can be achieved by breeding together each individual trait. Breeding together individual traits in maize and maintain this combination during breeding with a diverse pool of elite germplasm is a time-consuming and expensive process. A combination of traits can also be achieved by combining multiple traits at one location, or locus, in the genome, thereby simplifying the breeding process. One way to achieve this in through a single transgenic insertion containing multiple transgenes. The combination of multiple herbicide tolerance traits at a single locus in maize would provide a useful tool in weed control that is much simpler and less expensive to maintain during breeding with a diverse pool of elite germplasm.

The expression of a transgene in a transgenic plant, part, seed, or cell, and therefore its effectiveness, may be influenced by many different factors, such as the elements used in the transgene's expression cassette and the interaction of those elements. This is complicated further for a transgenic insertion containing two or more expression cassettes with each expression cassette having a transgene conferring a separate trait, also known as a multi-gene transgenic event. A commercially useful multi-gene transgenic event requires that each of the transgenes in the transgenic insertion express in the manner necessary for each trait. To achieve this, individual expression cassettes first are designed and tested in plants, and the best expression cassettes are selected for each trait. Next, the selected expression cassettes for one trait are combined with the selected expression cassettes for the other trait(s) into one construct, and the construct is tested to ensure that all the expression cassettes function well together and each transgene is properly expressed. Then, the selected combination of expression cassettes is used as a single transgenic insert to produce hundreds of multi-gene transgenic events, each event the result of a random insertion of the foreign DNA in a different genomic location.

Each transgenic event is unique. The unique events are then analyzed through multiple generations of plants to select a superior event for commercial use. The performance of an event in a transgenic plant, part, seed, or cell, and therefore its effectiveness, may be influenced by the genomic location of the transgenic insertion. Events can have the same transgenic insertion and nonetheless have different transgene expression levels and performance across tissues and developmental stages, in various germplasm, or under specific growth conditions. The creation of a multi-gene event for commercial use requires rigorous molecular characterization, greenhouse testing, and field trials over multiple years, in multiple locations, and under a variety of conditions so extensive agronomic, phenotypic, and molecular data may be collected. The resulting data must then be analyzed by scientists and agronomists to select an event that is useful for commercial purposes. The commercial multi-gene event can then be introgressed as a single locus having multiple herbicide tolerance traits into new germplasm using plant breeding methods.

BRIEF SUMMARY OF THE INVENTION

The invention provides recombinant DNA molecules comprising a sequence selected from the group consisting of SEQ ID NO:10, SEQ ID NO:9, SEQ ID NO:8, SEQ ID NO:7, SEQ ID NO:6, SEQ ID NO:5, SEQ ID NO:4, SEQ ID NO:3, SEQ ID NO:2, and SEQ ID NO:1. In one embodiment, the recombinant DNA molecule is derived from a plant, seed, or cell comprising maize event MON87429, a representative sample of seed comprising the event having been deposited as ATCC Accession No. PTA-124635. In another embodiment, the recombinant DNA molecule is in a plant, cell, seed, or plant part comprising maize event MON87429, a representative sample of seed comprising the event having been deposited as ATCC PTA-124635. In another embodiment, the recombinant DNA molecule is an amplicon diagnostic for the presence of maize event MON87429.

The invention provides a DNA construct comprising four expression cassettes, wherein the first expression cassette comprises in operable linkage (I) a ubiquitin promoter, leader, and intron from *Erianthus ravennae*, (II) a phosphinothricin N-acetyltransferase coding sequence, and (III) a fructose-bisphosphate aldolase 3' UTR from *Setaria italica*; the second expression cassette comprises in operable linkage (I) a ubiquitin promoter, leader, and intron from *Coix*

*lacryma-jobi*, (II) an albino and pale green 6 chloroplast transit peptide coding sequence from *Arabidopsis thaliana*, (III) a dicamba monooxygenase coding sequence, and (IV) a metallothionein-like protein 3' UTR from *Oryza sativa*; the third expression cassette comprises in operable linkage (I) a ubiquitin promoter, leader, and intron from *Arundo donax*, (II) a malate dehydrogenase chloroplast transit peptide coding sequence from *Arabidopsis thaliana*, (III) a FT_T protein coding sequence, and (IV) a no apical meristem protein 3' UTR from *Oryza sativa*; and the fourth expression cassette comprises in operable linkage (I) a CaMV 35S promoter and leader, (II) a chlorophyll a/b-binding protein leader from *Triticum aestivum*, (III) an actin 1 intron from *Oryza sativa*, (IV) a ShkG chloroplast transit peptide coding sequence from *Arabidopsis thaliana*, (V) a glyphosate tolerant 5-enolpyruvylshikimate-3-phosphate synthase coding sequence from *Agrobacterium* sp strain CP4, (VI) a male tissue specific siRNA target from *Zea mays*, and (VII) a glycine-rich RNA binding protein 3'UTR from *Oryza sativa*.

The invention provides a DNA molecule having a sufficient length of contiguous nucleotides of SEQ ID NO:10 to function as a DNA probe specific for SEQ ID NO:10 in a sample of DNA derived from a maize plant, maize seed, or maize cell. In one embodiment, the DNA probe comprises SEQ ID NO:13.

The invention provides a pair of DNA molecules comprising a first DNA molecule and a second DNA molecule, wherein the first and second DNA molecules each comprise a fragment SEQ ID NO:10 and function as DNA primers when used together in an amplification reaction with DNA containing maize event MON87429 to produce an amplicon diagnostic for maize event MON87429 in a sample. In one embodiment, at least one DNA primer comprises a fragment of a sequence selected from the group consisting of SEQ ID NO:7 and SEQ ID NO:8. In another embodiment, the first DNA molecule comprises SEQ ID NO:11 and the second DNA molecule comprises SEQ ID NO:12.

The invention provides a method of detecting the presence of maize event MON87429 in a sample of DNA derived from a maize plant, maize seed, or maize cell, the method comprising: contacting the sample with a DNA probe; subjecting the sample and the DNA probe to stringent hybridization conditions; and detecting hybridization of the DNA probe to a DNA molecule in the sample, wherein the hybridization of the DNA probe to the DNA molecule indicates the presence of maize event MON87429 in the sample of DNA.

The invention provides a method of detecting the presence of maize event MON87429 in a sample of DNA derived from a maize plant, maize seed, or maize cell, the method comprising: contacting the sample with a pair of DNA molecules that function as DNA primers; performing an amplification reaction sufficient to produce a DNA amplicon comprising a sequence selected from the group consisting of SEQ ID NO:10, SEQ ID NO:9, SEQ ID NO:8, SEQ ID NO:7, SEQ ID NO:6, SEQ ID NO:5, SEQ ID NO:4, SEQ ID NO:3, SEQ ID NO:2, and SEQ ID NO:1; and detecting the presence of the DNA amplicon, wherein the presence of the DNA amplicon indicates the presence of maize event MON87429 in the sample.

The invention provides a method of detecting the presence of maize event MON87429 in a sample derived from a maize plant, maize seed, or maize cell, the method comprising: contacting the sample with at least one antibody specific for at least one or more protein encoded by maize event MON87429; and detecting binding of the antibody to the protein in the sample, wherein the binding of the antibody to the protein indicates the presence of maize event MON87429 in the sample. In another embodiment, the method comprises additionally contacting the sample with at least a second antibody specific for a second protein encoded by maize event MON87429. In another embodiment, the method comprises additionally contacting the sample with at least a second antibody and a third antibody specific for a second protein and a third protein, respectively, encoded by maize event MON87429. In another embodiment, the method comprises additionally contacting the sample with at least a second antibody, a third antibody, and a fourth antibody specific for a second protein, a third protein, and a fourth protein, respectively, encoded by maize event MON87429.

The invention provides a kit for detecting the presence of maize event MON87429 comprising a DNA probe specific for SEQ ID NO:10, a pair of DNA primers that produce an amplicon diagnostic for maize event MON87429, or at least one antibody specific for at least one protein encoded by maize event MON87429.

The invention provides a plant, seed, cell, plant part, or commodity product comprising a DNA molecule comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. In one embodiment, the plant, seed, cell, or plant part is tolerant to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof. In another embodiment, the plant, seed, cell, or plant part is tolerant to quizalofop, haloxyfop, dicamba, 2,4-D, and glufosinate.

The invention provides a method for controlling weeds in a crop-growing area comprising planting maize comprising maize event MON87429 in the crop-growing area and applying to the crop-growing area, or any portion thereof, an effective amount of at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof, to control the weeds in the area without injuring the maize. In one embodiment, the method comprises applying at least two or more herbicides selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS) over a growing season. In another embodiment, the method comprises applying an herbicide selected from the group consisting of quizalofop, haloxyfop, dicamba, 2,4-D, glufosinate, and glyphosate, or any combination thereof. In one embodiment, the effective amount of dicamba is about 0.1 lb ae/acre to about 16 lb ae/acre over a growing season. In one embodiment, the effective amount of dicamba is about 0.5 lb ae/acre to about 2 lb ae/acre over a growing season. In one embodiment, the effective amount of glufosinate is about 0.1 lb ae/acre to about 16 lb ae/acre over a growing season. In one embodiment, the effective amount of glufosinate is about 0.4 lb ae/acre to about 1.59 lb ae/acre over a growing season. In one embodiment, the effective amount of 2,4-D is about 0.1 lb ae/acre to about 10 lb ae/acre over a growing season. In one embodiment, the effective amount of 2,4-D is about 0.75 lb ae/acre to 1.0 lb ae/acre over a growing season. In one embodiment, the effective amount of the FOP herbicide is about 0.01 lb ai/acre to about 1.0 lb ai/acre over a growing season. In one embodiment, the effective amount of the FOP herbicide is about 0.034 lb ai/acre to about 0.083 lb ai/acre of quizalofop over a growing season. In one embodiment, the effective amount of the FOP herbicide is about 0.018 ai/acre to about 0.07 lb ai/acre of haloxyfop over a growing season.

The invention provides a method for controlling volunteer maize comprising maize event MON87429 in an area comprising applying an herbicidally effective amount of at least one cyclohexanedione (DIM) herbicide, where the herbicide application prevents growth of maize comprising maize event MON87429. In one embodiment, the cyclohexanedione (DIM) herbicide is selected from the group consisting of clethodim, sethoxydim, and tralkoxydim.

The invention provides a method of producing a plant that is tolerant to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof, the method comprising: breeding a plant comprising maize event MON87429 with itself or a second plant to produce seed; and identifying progeny seed that comprise maize event MON87429. In one embodiment, identifying progeny seed that comprise maize event MON87429 is by growing the progeny seed to produce progeny plants; treating the progeny plants with an effective amount of at least one herbicide selected from the group consisting of quizalofop, haloxyfop, dicamba, 2,4-D, glufosinate, glyphosate, or any combination thereof; and selecting a progeny plant that is tolerant to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS). In one embodiment, identifying progeny seed that comprise maize event MON87429 is by detecting the presence of maize event MON87429 in a sample derived from the progeny seed. In one embodiment, identifying progeny seed that comprise maize event MON87429 is by detecting the presence of at least one protein encoded by maize event MON87429 in a sample derived from the progeny seed.

The invention provides a method of producing hybrid seed comprising: growing a plant comprising SEQ ID NO:10; applying an effective amount of glyphosate prior to or during the development of the male reproductive tissue of the plant thereby inducing male-sterility in the plant; fertilizing the plant with pollen from a second plant; and harvesting hybrid seed from the plant. In one embodiment, the glyphosate is applied prior to or during the development at an effective amount of about 0.25 lb ae/acre to about 11.0 lb ae/acre. In one embodiment, the glyphosate is applied prior to or during the development at an effective amount of about 0.5 lb ae/acre to about 2.5 lb ae/acre total in one or more applications. In one embodiment, the effective amount of glyphosate is applied at a developmental stage selected from the group consisting of the V4, V5, V6, V7, V8, V9, V10, V11, V12, V13, and V14 stage of maize plant development. The invention provides hybrid seed comprising SEQ ID NO:10 and produced by using the method of producing hybrid seed comprising: growing a plant comprising SEQ ID NO:10; applying an effective amount of glyphosate prior to or during the development of the male reproductive tissue of the plant thereby inducing male-sterility in the plant; fertilizing the plant with pollen from a second plant; and harvesting hybrid seed from the plant.

The invention provides a method of determining zygosity of a plant for maize event MON87429 comprising: contacting a sample comprising DNA derived from the plant with a primer set capable of producing a first amplicon diagnostic for the presence of maize event MON87429 and a second amplicon diagnostic for the wild-type maize genomic DNA not comprising maize event MON87429; performing a nucleic acid amplification reaction; detecting the first amplicon and the second amplicon, wherein the presence of both amplicons indicates the sample is heterozygous for maize event MON87429 and the presence of only the first amplicon indicates the sample is homozygous for maize event MON87429. In one embodiment, the primer set comprises SEQ ID NO:11 and SEQ ID NO:12.

The invention provides a method of improving tolerance to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof, in a maize plant comprising: (a) obtaining a DNA construct comprising four expression cassettes, wherein the first expression cassette comprises in operable linkage (I) a ubiquitin promoter, leader, and intron from *Erianthus ravennae*, (II) a phosphinothricin N-acetyltransferase coding sequence, and (III) a fructose-bisphosphate aldolase 3' UTR from *Setaria italica*; the second expression cassette comprises in operable linkage (I) a ubiquitin promoter, leader, and intron from *Coix lacrymajobi*, (II) an albino and pale green 6 chloroplast transit peptide coding sequence from *Arabidopsis thaliana*, (III) a dicamba monooxygenase coding sequence, and (IV) a metallothionein-like protein 3' UTR from *Oryza sativa*; the third expression cassette comprises in operable linkage (I) a ubiquitin promoter, leader, and intron from *Arundo donax*, (II) a malate dehydrogenase chloroplast transit peptide coding sequence from *Arabidopsis thaliana*, (III) a FT_T protein coding sequence, and (IV) a no apical meristem protein 3' UTR from *Oryza sativa*; and the fourth expression cassette comprises in operable linkage (I) a CaMV 35S promoter and leader, (II) a chlorophyll a/b-binding protein leader from *Triticum aestivum*, (III) an actin 1 intron from *Oryza sativa*, (IV) a ShkG chloroplast transit peptide coding sequence from *Arabidopsis thaliana*, (V) a glyphosate tolerant 5-enolpyruvylshikimate-3-phosphate synthase coding sequence from *Agrobacterium* sp strain CP4, (VI) a male tissue specific siRNA target from *Zea mays*, and (VII) a glycine-rich RNA binding protein 3'UTR from *Oryza sativa*; (b) inserting the DNA construct into the genome of a maize cell; (c) regenerating the maize cell into a maize plant; and (d) selecting a maize plant comprising the DNA construct. In one embodiment, selecting is by treating the maize plant with an effective amount of at least one herbicide selected from the group consisting of quizalofop, haloxyfop, dicamba, 2,4-D, glufosinate, or glyphosate. In one embodiment, the invention provides a maize plant, maize seed, or maize cell tolerant to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof, and obtainable by the method, wherein the maize plant, maize seed, or maize cell comprises the DNA construct. In a further embodiment, the maize plant, maize seed, or maize cell produced by the method comprises SEQ ID NO:10.

BRIEF DESCRIPTION OF THE SEQUENCES

Figure 1:
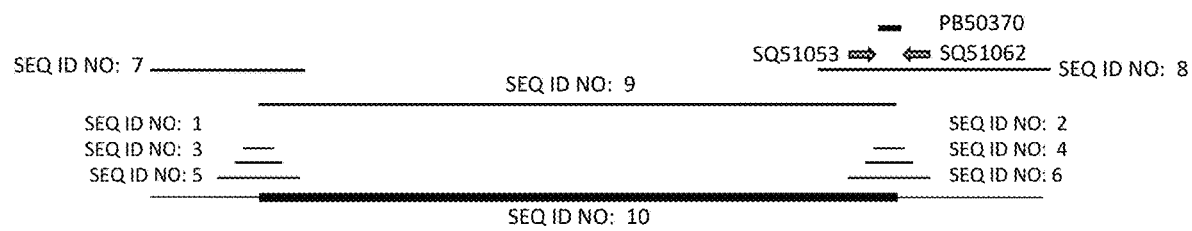
FIG. 1 represents the sequence of maize event MON87429. Horizontal lines correspond to the positions of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9 relative to SEQ ID NO:10; the horizontal arrows labeled SQ51062 (SEQ ID NO:11) and SQ51053 (SEQ ID NO:12) represent the approximate position of a pair of primers that can be used to detect maize event MON87429; and the horizontal line labeled PB50370 (SEQ ID NO:13) represents the approximate position of a DNA probe that can be used to detect maize event MON87429.

SEQ ID NO:1 is a thirty nucleotide DNA sequence representing the 5' junction of maize genomic DNA and the transgene insert. SEQ ID NO:1 corresponds to nucleotide positions 1015 to 1044 of SEQ ID NO:10.

SEQ ID NO:2 is a thirty nucleotide DNA sequence representing the 3' junction of maize genomic DNA and the transgene insert. SEQ ID NO:2 corresponds to nucleotide positions 15023 to 15052 of SEQ ID NO:10.

SEQ ID NO:3 is a sixty nucleotide DNA sequence representing the 5' junction of maize genomic DNA and the transgene insert. SEQ ID NO:3 corresponds to nucleotide positions 1000 to 1059 of SEQ ID NO:10.

SEQ ID NO:4 is a sixty nucleotide DNA sequence representing the 3' junction of maize genomic DNA and the transgene insert. SEQ ID NO:4 corresponds to nucleotide positions 15008 to 15067 of SEQ ID NO:10.

SEQ ID NO:5 is a one-hundred nucleotide DNA sequence representing the 5' junction of maize genomic DNA and the transgene insert. SEQ ID NO:5 corresponds to nucleotide positions 980 to 1079 of SEQ ID NO:10.

SEQ ID NO:6 is a one-hundred nucleotide DNA sequence representing the 3' junction of maize genomic DNA and the transgene insert. SEQ ID NO:6 corresponds to nucleotide positions 14988 to 15087 of SEQ ID NO:10.

SEQ ID NO:7 is a 1350 nucleotide DNA sequence representing 1029 nucleotides of the 5' flanking maize genomic DNA and 321 nucleotides of the 5' end of the transgene insert.

SEQ ID NO:8 is a 1069 nucleotide DNA sequence representing 38 nucleotides of the 3' end of the transgene insert and 1031 nucleotides of the 3' flanking maize genomic DNA.

SEQ ID NO:9 is a 14008 nucleotide DNA sequence corresponding to the transgene insert of the maize MON87429 event.

SEQ ID NO:10 is a 16068 nucleotide DNA sequence corresponding to the maize MON87429 event; the sequence contains the 5' flanking genomic DNA sequence from positions 1 to 1029, the transgenic DNA insert from positions 1030 to 15037, and the 3' flanking genomic DNA sequence from positions 15038 to 16068.

SEQ ID NO:11 is a 29 nucleotide DNA sequence corresponding to a primer referred to as SQ51062 and used to identify maize MON87429 event DNA in a sample; it corresponds to positions 15038 to 15066 of SEQ ID NO:10.

SEQ ID NO:12 is a 17 nucleotide DNA sequence corresponding to a primer referred to as SQ51053 and used to identify maize MON87429 event DNA in a sample; it corresponds to positions 14987 to 15003 of SEQ ID NO:10.

SEQ ID NO:13 is a 16 nucleotide DNA sequence corresponding to a probe referred to as PB50370 and used to identify maize MON87429 event DNA in a sample; it corresponds to positions 15009 to 15024 of SEQ ID NO:10.

DETAILED DESCRIPTION OF THE INVENTION

The following definitions and methods are provided to better define the invention and to guide those of ordinary skill in the art in the practice of the invention. Unless otherwise noted, terms are to be understood according to conventional usage by those of ordinary skill in the relevant art.

Plant transformation techniques are used to insert foreign DNA (also known as transgenic DNA) randomly into a chromosome of the genome of a cell to produce a genetically engineered cell, also referred to as "transgenic" or "recombinant" cell. Using this technique, many individual cells are transformed, each resulting in a unique transgenic event due to the random insertion of the foreign DNA into the genome. A transgenic plant is then regenerated from each individual transgenic cell. This results in every cell of the transgenic plant containing the uniquely inserted transgenic event as a stable part of its genome. This transgenic plant can then be used to produce progeny plants, each containing the unique transgenic event. Maize event MON87429 was produced by: (i) transformation of thousands of maize cells with a DNA construct that includes four expression cassettes (each expression cassette having been selected after individual testing followed by testing in combination with the other three expression cassettes), (ii) regeneration of a population of transgenic plants each containing a unique transgenic event, and (iii) rigorous multi-year event selection involving the testing and analysis of molecular characteristics, herbicide tolerance efficacy, and agronomic properties in a variety of genetic backgrounds for thousands of events through tens of thousands of plants. Maize event MON87429 was thus produced and selected as a uniquely superior event useful for broad-scale agronomic commercial purposes.

As used herein, a "transgenic event" or an "event" is a DNA molecule created by the act of inserting a transgenic DNA molecule into the genomic DNA of a plant cell using plant transformation methods known in the art. This insertion creates a new, transgenic genomic DNA sequence that consists of the inserted foreign DNA (referred to as the "transgenic insert") and the genomic DNA immediately adjacent to, or "flanking", the transgenic insert on either side of the insertion location (referred to as the "flanking DNA"). The DNA sequence of an event is unique to and specific for the event and can be readily identified when compared to other DNA sequences, such as that of other events or untransformed maize genomic DNA. Maize event MON87429 has the new and unique DNA sequence provide as SEQ ID NO:10, which contains the transgenic insert sequence provided as SEQ ID NO:9 and the 5' and 3' flanking DNA sequence provided in SEQ ID NO:7 and SEQ ID NO:8, respectively. Maize event MON87429 is thus a DNA molecule that is an integral part of the chromosome of transgenic maize cells and plants comprising the event and as such is static and may be passed on to progeny cells and plants.

The present invention also provides progeny of the original transformed cell and plant that comprise maize event MON87429. Such progeny may be produced by cell tissue culture, by selfing of a maize plant comprising the maize event MON87429, or by sexual outcrossing between a maize plant comprising maize event MON87429 and another plant that does or does not contain the event. Such other plant may be a transgenic plant comprising the same or different event(s) or a nontransgenic plant, such as one from a different variety. Maize event MON87429 is passed from the original parent through each generation to the progeny.

As used herein, the term "maize" means *Zea mays* (also referred to as corn) and includes all plant varieties that can be bred with *Zea mays*.

Figure 2:
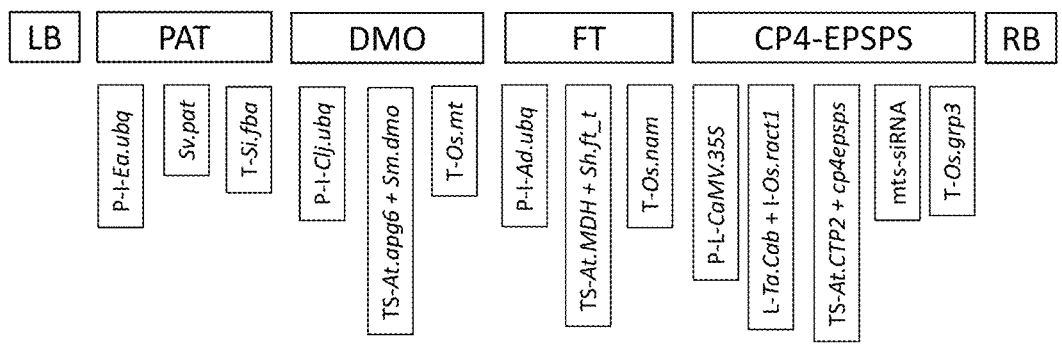
FIG. 2 represents the four expression cassettes of maize event MON87429 relative to SEQ ID NO:9 with their respective genetic elements labeled as described in Table 1.
Figure 3:
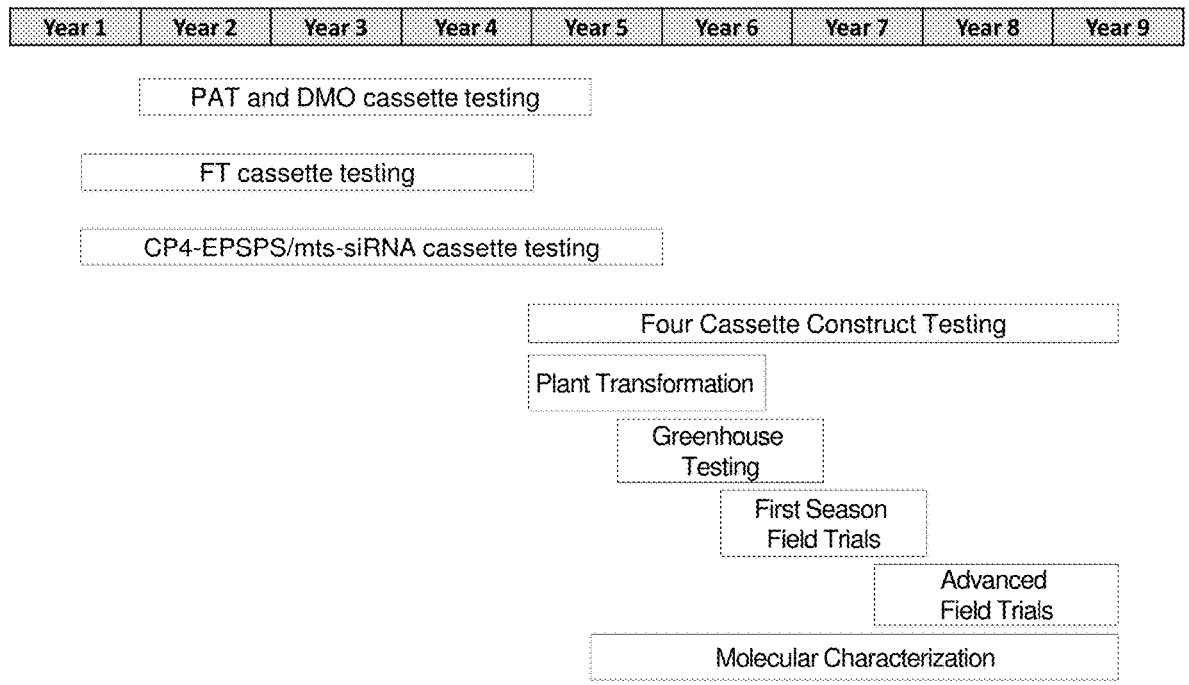
FIG. 3 represents the creation, testing, characterization, and selection of the MON87429 event as described herein. All times are approximate.

The invention provides maize event MON87429, which provides to maize cells, plants, and seeds that comprise the event tolerance to inhibitors of acetyl CoA carboxylase (ACCase) in the aryloxyphenoxy propionate (FOP) group such as quizalofop and haloxyfop; synthetic auxins such as dicamba and 2,4-D; inhibitors of glutamine synthetase such as glufosinate; and the 5-enolpyruvylshikimate-3-phosphate synthase (EPSPS) inhibitor glyphosate. Maize event MON87429 contains four expression cassettes. As used herein, an "expression cassette" or "cassette" is a recombinant DNA molecule comprising a combination of distinct elements that are to be expressed by a transformed cell. Table 1 provides a list of the elements contained in SEQ ID NO:10 and as illustrated in FIG. 2.

TABLE 1

Description of maize event MON87429

| Element | Position in SEQ ID NO: 10 | Description |
|---|---|---|
| 5' Flanking DNA | 1-1029 | DNA sequence flanking the 5' end of the transgenic insert |
| Left Border Region | 1030-1288 | DNA region from *Agrobacterium tumefaciens* containing the left border sequence |
| Intervening Sequence | 1289-1359 | Sequence used in DNA cloning |
| P-Ea.ubq | 1360-3541 | Promoter, 5' UTR, and intron sequences of a ubiquitin gene from *Erianthus ravennae* |
| Intervening Sequence | 3542-3546 | Sequence used in DNA cloning |
| CS-Sv.pat | 3547-4098 | Coding sequence for the phosphinothricin N-acetyltransferase (PAT) protein |
| T-Si.fba | 4099-4475 | 3' UTR sequence of the fructose-bisphosphate aldolase gene from *Setaria italica* |
| Intervening Sequence | 4476-4537 | Sequence used in DNA cloning |
| P-Clj.ubq | 4538-6463 | Promoter, 5' UTR, and intron sequences of a ubiquitin gene from *Coix lacryma-jobi* |
| Intervening Sequence | 6464-6473 | Sequence used in DNA cloning |
| TS-At.apg6 | 6474-6677 | Codon optimized targeting sequence of the Albino and pale green 6 gene from *Arabidopsis thaliana* |
| CS-Sm.dmo | 6678-7700 | Coding sequence for the dicamba monooxygenase (DMO) protein |
| Intervening Sequence | 7701-7708 | Sequence used in DNA cloning |
| T-Os.mt | 7709-8008 | 3' UTR sequence of the metallothionein-like protein from *Oryza sativa* |
| Intervening Sequence | 8009-8016 | Sequence used in DNA cloning |
| P-Ad.ubq | 8017-9973 | Promoter, 5' UTR, and intron sequences of a ubiquitin gene from *Arundo donax* |
| Intervening Sequence | 9974-9986 | Sequence used in DNA cloning |
| TS-At.mdh | 9987-10229 | Sequence of the transit peptide of the malate dehydrogenase gene from *Arabidopsis thaliana* |
| CS-Sh.ft_t | 10230-11117 | Coding sequence for the FT_T protein |
| Intervening Sequence | 11118-11132 | Sequence used in DNA cloning |
| T-Os.nam | 11133-11649 | 3' UTR sequence of the no apical meristem protein from *Oryza sativa* |
| Intervening Sequence | 11650-11655 | Sequence used in DNA cloning |
| P-CaMV.35S | 11656-11979 | Promoter and leader from the 35S RNA of cauliflower mosaic virus |
| Intervening Sequence | 11980-12001 | Sequence used in DNA cloning |
| L-Ta.cab | 12002-12062 | 5' UTR leader sequence from chlorophyll a/b-binding protein of *Triticum aestivum* |
| Intervening Sequence | 12063-12078 | Sequence used in DNA cloning |
| I-Os.ract1 | 12079-12558 | Intron and UTR sequence of the Actin 1 protein from *Oryza sativa* |
| Intervening Sequence | 12559-12567 | Sequence used in DNA cloning |
| TS-At.CTP2 | 12568-12795 | Transit peptide sequence of the ShkG gene from *Arabidopsis thaliana* |
| CS-cp4epsps | 12796-14163 | Coding sequence for the 5-enolpyruvylshikimate-3-phosphate synthase (CP4-EPSPS) protein |

TABLE 1-continued

Description of maize event MON87429

| Element | Position in SEQ ID NO: 10 | Description |
| --- | --- | --- |
| Intervening Sequence | 14164-14169 | Sequence used in DNA cloning |
| mts-siRNA | 14170-14370 | Sequence of the male tissue specific siRNA target |
| Intervening Sequence | 14371-14378 | Sequence used in DNA cloning |
| T-Os.grp3 | 14379-14989 | 3' UTR sequence of the glycine-rich RNA-binding protein (Grp3) gene from *Oryza sativa* |
| Intervening Sequence | 14990-15030 | Sequence used in DNA cloning |
| Right Border Region | 15031-15037 | DNA region from *Agrobacterium tumefaciens* containing the right border sequence |
| 3' Flanking DNA | 15038-16068 | Flanking DNA |

As used herein, the term "recombinant" refers to a non-natural DNA, protein, or organism that would not normally be found in nature and was created by human intervention. As used herein, a "recombinant DNA molecule" is a DNA molecule comprising a combination of DNA molecules that would not naturally occur together and is the result of human intervention, for example, a DNA molecule that is comprised of a combination of at least two DNA molecules heterologous to each other, such as a DNA molecule that comprises a transgene and the plant genomic DNA adjacent to the transgene. An example of a recombinant DNA molecule is a DNA molecule comprising at least one sequence selected from SEQ ID NO:1-10. As used herein, a "recombinant plant" is a plant that would not normally exist in nature, is the result of human intervention, and contains a transgenic DNA molecule. As a result of such genomic alteration, the recombinant plant is something new and distinctly different from the related wild-type plant. An example of a recombinant plant is a maize plant containing the maize event MON87429.

As used herein, the term "transgene" refers to a DNA molecule artificially incorporated into an organism's genome as a result of human intervention, such as by plant transformation methods. A transgene may be heterologous to the organism. The term "transgenic insert" as used herein refers to the foreign DNA inserted by plant transformation techniques into the maize genome to produce maize event MON87429. The sequence for the transgenic insert of maize event MON87429 is provided as SEQ ID NO:9. The term "transgenic" refers to comprising a transgene, for example a "transgenic plant" refers to a plant comprising a transgene.

As used herein, the term "heterologous" refers to a first molecule not normally associated with a second molecule or an organism in nature. For example, a DNA molecule may be from a first species and inserted into the genome of a second species. The DNA molecule would thus be heterologous to the genome and the organism.

As used herein, the term "chimeric" refers to a single DNA molecule produced by fusing a first DNA molecule to a second DNA molecule, where neither first nor second DNA molecule would normally be found in that configuration fused to the other. The chimeric DNA molecule is thus a new DNA molecule not normally found in nature. An example of a chimeric DNA molecule is a DNA molecule comprising at least one sequence selected from SEQ ID NO:1-10.

As used herein, the term "isolated" refers to separating a molecule from other molecules that are normally associated with it in its native or natural state. The term "isolated" thus may refer to a DNA molecule that has been separated from other DNA molecule(s) that it is associated with it in its native or natural state. Such a DNA molecule may be present in a recombined state, such as a recombinant DNA molecule. Thus, a DNA molecule removed from its natural state and fused to another DNA molecule with which it is not normally associated would be an isolated DNA molecule. Such an isolated DNA molecule could result from the use of biotechnology techniques, such as making recombinant DNA or integrating a foreign DNA molecule into the chromosome of a cell, plant, or seed.

The invention provides DNA molecules and their corresponding DNA sequences. As used herein, the terms "DNA" and "DNA molecule" refer to a deoxyribonucleic acid (DNA) molecule. A DNA molecule may be of genomic or synthetic origin and is by convention from the 5' (upstream) end to the 3' (downstream) end. As used herein, the term "DNA sequence" refers to the nucleotide sequence of a DNA molecule. The nomenclature used is that required by Title 37 of the United States Code of Federal Regulations § 1.822 and set forth in the tables in WIPO Standard ST.25 (1998), Appendix 2, Tables 1 and 3. By convention, the DNA sequences of the invention and fragments thereof are disclosed with reference to only one strand of the two complementary DNA sequence strands. By implication and intent, the complementary sequences of the sequences provided here (the sequences of the complementary strand), also referred to in the art as the reverse complementary sequences, are within the scope of the invention and are expressly intended to be within the scope of the subject matter claimed. Thus, as used herein references to SEQ ID NO:1-10 and fragments thereof include and refer to the sequence of the complementary strand and fragments thereof.

As used herein, the term "fragment" refers to a smaller piece of a whole. For example, fragments of SEQ ID NO:10 would include sequences that are at least about 10 consecutive nucleotides, at least about 11 consecutive nucleotides, at least about 12 consecutive nucleotides, at least about 13 consecutive nucleotides, at least about 14 consecutive nucleotides, at least about 15 consecutive nucleotides, at least about 16 consecutive nucleotides, at least about 17 consecutive nucleotides, at least about 18 consecutive nucleotides, at least about 19 consecutive nucleotides, at least about 20 consecutive nucleotides, at least about 25 consecutive nucleotides, at least about 30 consecutive nucleotides, at least about 35 consecutive nucleotides, at least about 40 consecutive nucleotides, at least about 45 consecutive nucleotides, at least about 50 consecutive nucleotides, at least about 60 consecutive nucleotides, at least about 70 consecutive nucleotides, at least about 80 consecutive nucleotides, at least about 90 consecutive nucleotides, or at least about 100 consecutive nucleotides of the complete sequence of SEQ ID NO:10.

The DNA sequence for the transgenic insert of maize event MON87429 is provided as SEQ ID NO:9. The DNA sequence of the transgenic insert and the maize genomic DNA flanking each side of the transgenic insert is provided as SEQ ID NO:10. The DNA sequences of a portion of flanking DNA and the 5' end of the transgenic insert are provided as SEQ ID NO:1, SEQ ID NO:3, SEQ ID NO:5, and SEQ ID NO:7. The DNA sequences of a portion of flanking DNA and the 3' end of the transgenic insert are provided as SEQ ID NO:2, SEQ ID NO:4, SEQ ID NO:6, and SEQ ID NO:8.

The DNA sequence of the region spanning the connection by phosphodiester bond linkage of one end of the transgenic insert to the flanking maize genomic DNA is referred to herein as a "junction". A junction is the connection point of the transgenic insert and flanking DNA as one contiguous molecule. One junction is found at the 5' end of the transgenic insert and the other is found at the 3' end of the transgenic insert, referred to herein as the 5' and 3' junction, respectively. A "junction sequence" refers to a DNA sequence of any length that spans the 5' or 3' junction of an event. Junction sequences of maize event MON87429 are apparent to one of skill in the art using SEQ ID NO:10. Examples of junction sequences of maize event MON87429 are provided as SEQ ID NO:1-8. FIG. 1 illustrates the physical arrangement of SEQ ID NO:1-10 arranged from 5' to 3'. The junction sequences of maize event MON87429 may be present as part of the genome of a plant, seed, or cell containing maize event MON87429. The identification of any one or more of SEQ ID NO:1-8 or 10 in a sample from a plant, plant part, seed, or cell indicates that the DNA was obtained from maize containing maize event MON87429 and is diagnostic for the presence of maize event MON87429.

The plants, seeds, cells, plant parts, and commodity products of the invention may be used for detection of DNA or protein molecules indicative of the presence of maize event MON87429. Provided are exemplary DNA molecules that can be used either as primers or probes for detecting the presence of maize event MON87429 in a sample. Such primers or probes are specific for a target nucleic acid sequence and as such are useful for the identification of maize event MON87429 by the methods described here. Detection of the presence of maize event MON87429 may be done by using methods known in the art, such as thermal amplification of nucleic acid or nucleic acid hybridization techniques (such as northern blotting and southern analysis).

A "primer" is a DNA molecule that is designed for use in annealing or hybridization methods that involve an amplification reaction. An amplification reaction is an in vitro reaction that amplifies template DNA to produce an amplicon. As used herein, an "amplicon" is a DNA molecule that has been synthesized using amplification techniques. Amplicons of the invention have a DNA sequence comprising one or more of SEQ ID NO:1-10, or fragments thereof. A pair of primers may be used with template DNA, such as a sample of maize genomic DNA, in an amplification reaction, such as polymerase chain reaction (PCR), to produce an amplicon, where the amplicon produced would have a DNA sequence corresponding to sequence of the template DNA located between the two sites where the primers hybridized to the template. A primer is typically designed to hybridize to a complementary target DNA strand to form a hybrid between the primer and the target DNA strand. The presence of a primer is a point of recognition by a polymerase to begin extension of the primer using as a template the target DNA strand. Primer pairs refer to use of two primers binding opposite strands of a double stranded nucleotide segment for the purpose of amplifying the nucleotide segment between them. Examples of primer sequences are provided as SEQ ID NO:11 (SQ51062) and SEQ ID NO:12 (SQ51053). The primer pair provided as SEQ ID NO:11 and SEQ ID NO:12 are useful as a first DNA molecule and a second DNA molecule, where the first DNA molecule is a fragment of the transgenic insert DNA sequence of SEQ ID NO:10 and the second DNA molecule is a fragment of the flanking DNA sequence of SEQ ID NO:10, and each are of sufficient length to function as DNA primers when used together in an amplification reaction with DNA containing maize event MON87429 to produce an amplicon diagnostic for maize event MON87429 in a sample. Primer pairs of the present invention may in certain embodiments also be defined as comprising a first and second DNA molecule, wherein the first DNA molecule is a fragment of the maize genomic portion of SEQ ID NO:10 and the second DNA molecule is a fragment of the transgene portion of SEQ ID NO:10, and each are of sufficient length to function as DNA primers when used together in an amplification reaction with DNA containing maize event MON87429 to produce an amplicon diagnostic for maize event MON87429 in a sample.

A "probe" is a nucleic acid molecule that is complementary to a strand of a target nucleic acid and useful in hybridization detection methods. Probes according to the invention include not only deoxyribonucleic or ribonucleic acids but also polyamides and other probe materials that bind specifically to a target DNA sequence and the detection of such binding can be useful in detecting the presence or absence of the target DNA sequence. A probe may be attached to a conventional detectable label or reporter molecule, such as a radioactive isotope, ligand, chemiluminescent agent, or enzyme. An exemplary DNA sequence useful as a probe for detecting maize event MON87429 is provided as SEQ ID NO:13 (PB50370).

Methods for designing and using primers and probes are well known in the art. DNA molecules comprising the full length of or fragments of SEQ ID NO:1-10 are useful as primers and probes for detecting maize event MON87429 and can readily be designed by one of skill in the art using the sequences provided herein.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from maize event MON87429 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by M R Green and J Sambrook, *Molecular cloning: a laboratory manual*, 4$^{th}$ Edition, Cold Spring Harbor Laboratory Press, Cold Spring Harbor, N.Y. (2012). As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, two molecules exhibit "complete complementarity" if when aligned every nucleotide of the first molecule is complementary to every nucleotide of the second molecule. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

Appropriate stringency conditions that promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Provided are proteins that can be used to produce antibodies for detecting the presence of maize event MON87429 in a sample. Such antibodies are specific for one or more of the proteins that are encoded by maize event MON87429. The DNA sequence encoding such proteins is provided in SEQ ID NO:10 and the start positions and stop positions of the coding sequence are indicated in Table 1. The DNA sequence encoding each protein and the protein encoded by the sequence are useful to produce antibodies for detecting the presence of maize event MON87429 by the methods described here. Detection of the presence of maize event MON87429 may be done by using any protein detection techniques known in the art, such as western blotting, immuno-precipitation, enzyme-linked immunosorbent assay (ELISA), antibody attachment to a detectable label or reporter molecule (such as a radioactive isotope, ligand, chemiluminescent agent, or enzyme), or enzymatic action on a reporter molecule. One method provides for contacting a sample with an antibody that binds to the DMO, PAT, FT_T, or CP4-EPSPS protein encoded by maize event MON87429 and then detecting the presence or absence of antibody binding. The binding of such antibody is diagnostic for the presence of one or more proteins encoded by maize event MON87429.

Protein and nucleic acid detection kits for detecting the presence of maize event MON87429 are provided. Variations on such kits can also be developed using the compositions and methods disclosed herein and the methods well known in the art of protein and nucleic acid detection. Protein and nucleic acid detection kits can be applied to methods for breeding with plants containing maize event MON87429. Such kits contain primers or probes comprising fragments of SEQ ID NO:1-10 or antibodies specific for a protein encoded by maize event MON87429.

One example of a detection kit comprises at least one DNA molecule of sufficient length of contiguous nucleotides of SEQ ID NO:10 to function as a DNA probe useful for detecting the presence or absence of maize event MON87429 in a sample. An exemplary DNA molecule sufficient for use as a probe is one comprising the sequence provided as SEQ ID NO:13. Other probes may be readily designed by one of skill in the art. Another example of a detection kit comprises at least one primer pair useful for producing an amplicon useful for detecting the presence or absence of maize event MON87429 in a sample. Such a method may also include sequencing the amplicon or a fragment thereof. Exemplary DNA molecules sufficient for use as a primer pair are ones comprising the sequences provided as SEQ ID NO:11 and SEQ ID NO:12, respectively. Other primer pairs may be readily designed by one of skill in the art. Kits of the invention may optionally also comprise reagents for performing the detection or diagnostic reactions described herein. Another example of a detection kit comprises at least one antibody specific for at least one protein encoded by maize event MON87429. For example, such a kit may utilize a lateral flow strip comprising reagents activated when the tip of the strip is contacted with an aqueous solution. Exemplary proteins sufficient for use in antibody production are ones encoded by the sequence provided as SEQ ID NO:10, or any fragment thereof.

The invention provides maize plants, progeny, seeds, cells, and plant parts containing maize event MON87429, and commodity products produced using these. The plants, progeny, seeds, cells, plant parts, and commodity products of the invention contain a detectable amount of DNA having at least one of the sequences provided as SEQ ID NO:1-8 and SEQ ID NO:10.

Plants, progeny, seeds, cells, and plant parts of the invention may also contain one or more additional transgenic traits, particularly those introduced by crossing a maize plant containing maize event MON87429 with another plant containing the additional transgenic trait(s). Such traits include but are not limited to increased insect resistance, increased water use efficiency, increased yield performance, increased drought resistance, increased seed quality, improved nutritional quality, hybrid seed production, and/or increased herbicide tolerance, in which the trait is measured with respect to a maize plant lacking such transgenic trait.

Plants of the invention may be used to produce progeny that contain maize event MON87429. As used herein, "progeny" includes any plant, seed, and cell comprising maize event MON87429 inherited from an ancestor plant, indicated by the plant comprising a DNA molecule having at least one sequence selected from SEQ ID NO:1-8 and SE ID NO:10. Plants, seeds, and cells may be homozygous or heterozygous for maize event MON87429. Progeny plants may be grown from seeds produced by a maize plant containing maize event MON87429 or from seeds produced by a maize plant fertilized with pollen containing maize event MON87429.

As used herein, a "plant part" of the invention is any part from a plant containing maize event MON87429. Plant parts include but are not limited to tissue samples, pollen, ovule, pod, flower, roots, stems, fibers, and leaves in whole or part. Plant parts may be viable or nonviable.

The invention provides a commodity product that is produced from plants containing maize event MON87429.

Commodity products of the invention contain a detectable amount of DNA comprising a DNA sequence selected from the group consisting of SEQ ID NO:1-10. As used herein, a "commodity product" refers to any composition or product which is comprised of material from plant, seed, cell, or plant part comprising maize event MON87429. Commodity products include but are not limited to processed seeds, grains, plant parts, and meal. A commodity product of the invention will contain a detectable amount of DNA corresponding to maize event MON87429. Detection of one or more of this DNA in a sample may be used for determining the content or the source of the commodity product. Any standard method of detection for DNA molecules may be used, including methods of detection disclosed herein.

Maize event MON87429 contains four expression cassettes that together provide tolerance to inhibitors of acetyl CoA carboxylase (ACCase) in the aryloxyphenoxy propionate (FOP) group; synthetic auxins; inhibitors of glutamine synthetase; and inhibitors of 5-enolpyruvylshikimate-3-phosphate synthase (EPSPS).

As used herein, inhibitors of acetyl CoA carboxylase (ACCase) in the aryloxyphenoxy propionate (FOP) group (referred to as "FOP herbicide(s)") include, but are not limited to, clodinafop, clodinafop-ethyl, clodinafop-propargyl, cyhalofop, cyhalofop-butyl, diclofop, diclofop-methyl, diclofop-P, diclofop-P-methyl, fenoxaprop, fenoxaprop-P, fenoxaprop-P-ethyl, fenthiaprop, fluazifop, fluazifop-butyl, fluazifop-P, fluazifop-P-butyl, fluroxypyr, haloxyfop, haloxyfop.etotyl, haloxyfop-methyl, haloxyfop-P, haloxyfop-P-methyl, isoxapyrifop, metamifop, propaquizafop, quizalofop, quizalafop-ethyl, quizalofop-P, quizalafop-P-ethyl, quizalafop-P-tefuryl, and trifop.

As used herein, synthetic auxins include, but are not limited to, benzoic acid herbicides, phenoxy acid herbicides, arylpicolinate herbicides, and pyridinyloxy acid herbicides. Examples of a benzoic acid herbicides include, but are not limited to, dicamba (3,6-dichloro-2-methoxybenzoic acid), dicamba salts, dicamba-butotyl, dicamba-diglycolamine salt, dicamba-dimethylammonium, dicamba-diethanolammonium, dicamba-isopropylammonium, dicamba-potassium, dicamba-sodium, and dicamba-trolamine. Examples of phenoxy acid herbicides are 2,4-D (2,4-dichlorophenoxyacetic acid), 2,4-D-butotyl, 2,4-D-butyl, 2,4-D-choline, 2,4-D-dimethylammonium, 2,4-D-diolamin, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-potassium, 2,4-D-sodium, 2,4-D-triisopropanolammonium, 2,4-D-trolamine, clomeprop, dichlorprop, fenoprop, MCPA, MCPA-butotyl, MCPA-dimethylammonium, MCPA-2-ethylhexyl. MCPA-isopropylammonium, MCPA-potassium, MCPA-sodium, MCPA-thioethyl, 2,4-DB, MCPB, MCPB-methyl, MCPB-ethyl-sodium, and mecoprop. Examples of arylpicolinate herbicides are halauxifen, halauxifen-methyl, and florpyrauxifen-benzyl. Examples of pyridinyloxy acid herbicides are triclopyr, fluroxypyr, aminopyralid, clopyralid, and picloram.

As used herein, inhibitors of glutamine synthetase include, but are not limited to, phosphinothricin, glufosinate, glufosinate salts, glufosinate-ammonium, glufosinate-sodium, glufosinate-P, L-glufosinate-ammonium, and L-glufosinate-sodium.

As used herein, inhibitors of 5-enolpyruvylshikimate-3-phosphate synthase (EPSPS) include, but are not limited to, glyphosate, glyphosate salts, glyphosate-isopropylammonium, glyphosate-ammonium, glyphosate-dimethylammonium, glyphosate-trimesium (=sulfosate), glyphosate-diammonium, glyphosate-potassium, and glyphosate-sodium.

As used herein, "herbicide tolerant" or "herbicide tolerance" or "tolerance" means the ability to be wholly or partially unaffected by the presence or application of one or more herbicide(s), for example to resist the toxic effects of an herbicide when applied. A cell, seed, or plant is "herbicide tolerant" or has "improved tolerance" if it can maintain at least some normal growth or phenotype in the presence of one or more herbicide(s). A trait is an herbicide tolerance trait if its presence can confer improved tolerance to an herbicide upon a cell, plant, or seed as compared to the wild-type or control cell, plant, or seed. Crops comprising an herbicide tolerance trait can continue to grow in the presence of the herbicide and may be minimally affected by the presence of the herbicide. A protein confers "herbicide tolerance" if expression of the protein can confer improved tolerance to an herbicide upon a cell, plant, or seed as compared to the wild-type or control cell, plant, or seed. Examples of herbicide tolerance proteins are phosphinothricin N-acetyltransferase, dicamba monooxygenase coding sequence, the FT_T protein, and glyphosate tolerant 5-enolpyruvylshikimate-3-phosphate synthase coding sequence from *Agrobacterium* sp strain CP4. Herbicide tolerance may be complete or partial insensitivity to a particular herbicide and may be expressed as a percent (%) tolerance or insensitivity to a particular herbicide.

As used herein, a "weed" is any undesired plant. A plant may be considered generally undesirable for agriculture or horticulture purposes (for example, *Amaranthus* species) or may be considered undesirable in a particular situation (for example, a crop plant of one species in a field of a different species, also known as a volunteer plant). Weeds are commonly known in the art and vary by geography, season, growing environment, and time. Lists of weed species are available from agricultural and scientific societies and efforts (such as the Weed Science Society of America, the Canadian Weed Science Society, the Brazilian Weed Science Society, the International Weed Science Society, and the International Survey of Herbicide Resistant Weeds), government agencies (such as the United States Department of Agriculture and the Australia Department of the Environment and Energy), and industry and farmer associations (such as the National Corn Growers Association).

The invention provides methods for controlling weeds in an area for maize cultivation by applying at least one herbicide selected from the group consisting of (i) inhibitors of acetyl CoA carboxylase (ACCase) in the aryloxyphenoxy propionate (FOP) group such as quizalofop and haloxyfop; (ii) synthetic auxins such as dicamba and 2,4-D; (iii) inhibitors of glutamine synthetase such as glufosinate; and (iv) the 5-enolpyruvylshikimate-3-phosphate synthase (EPSPS) inhibitor glyphosate, where seeds or plants comprising maize event MON87429 are planted in the area before, at the time of, or after applying the herbicide and the herbicide application prevents or inhibits weed growth and does not injure the maize plants. The plant growth area may or may not comprise weed plants at the time of herbicide application. The herbicide(s) used in the methods of the invention can be applied alone or in combination with one or more herbicide(s) during the growing season. The herbicide(s) used in the methods of the invention can be applied in combination with one or more herbicide(s) temporally (for example, as a tank mixture or in sequential applications), spatially (for example, at different times during the growing season including before and after maize seed planting), or both. For example, a method for controlling weeds is provided that consists of planting seed comprising maize event MON87429 in an area and applying an herbicidally effective amount over the growing season of one or more of dicamba, glufosinate, glyphosate, 2,4-D, or a FOP herbicide, alone or in any combination with another herbicide, for the purpose of controlling weeds in the area without injuring the plants containing maize event MON87429. Such application of herbicide(s) may be pre-planting (any time prior to planting seed containing maize event MON87429, including for burn-down purposes, that is application to emerging or existing weeds prior to seed plant), pre-emergence (any time after seed containing maize event MON87429 is planted and before plants containing maize event MON87429 emerge), or post-emergence (any time after plants containing maize event MON87429 emerge). Multiple applications of one or more herbicides, or a combination of herbicides together or individually, may be used over a growing season, for example, two applications (such as a pre-planting application and a post-emergence application, or a pre-emergence application and a post-emergence application) or three or more applications (such as a pre-planting application and two post-emergence applications).

Herbicide application in practicing the methods of the invention may be at the recommended commercial rate or any fraction or multiple thereof, such as twice the recommended commercial rate. Herbicide rates may be expressed as acid equivalent per pound per acre (lb ae/acre) or active ingredient per pound per acre (lb ai/acre), depending on the herbicide and the formulation. The herbicide application may be the recommended commercial rate or a fraction or multiple thereof. The use of acres in the herbicide application rates as provided herein is merely instructive; herbicide application rates in the equivalent dosages to any rate provided herein may be used for areas larger or smaller than an acre. The herbicide application comprises at least one herbicide selected from the group consisting of (i) inhibitors of acetyl CoA carboxylase (ACCase) in the aryloxyphenoxy propionate (FOP) group such as quizalofop and haloxyfop; (ii) synthetic auxins such as dicamba and 2,4-D; (iii) inhibitors of glutamine synthetase such as glufosinate; and (iv) the 5-enolpyruvylshikimate-3-phosphate synthase (EPSPS) inhibitor glyphosate. The plant growth area may or may not comprise weed plants at the time of herbicide application. An herbicidally effective amount of the FOP herbicides for use in the area for controlling weeds should consist of a range from about 0.01 lb ai/acre to about 1.0 lb ai/acre over a growing season (for example, quizalofop could be applied at a rate of about 0.034 lb ai/acre to about 0.083 lb ai/acre and haloxyfop could be applied at a rate of about 0.018 ai/acre to about 0.07 lb ai/acre). An herbicidally effective amount of the synthetic auxin phenoxy acid herbicides for use in the area for controlling weeds should consist of a range from about 0.1 lb ae/acre to about 10 lb ae/acre over a growing season (for example, 2,4-D could be applied at a rate of about 0.75 lb ae/acre to 1.0 lb ae/acre). An herbicidally effective amount of the synthetic auxin pyridinyloxy acid herbicides for use in the area for controlling weeds should consist of a range from about 0.05 lb ae/acre to about 5.0 lb ae/acre over a growing season (for example, fluroxypyr could be applied at a rate of about 0.14 lb ae/acre to about 0.49 lb ae/acre). An herbicidally effective amount of a synthetic auxin benzoic acid herbicide for use in the area for controlling weeds should consist of a range from about 0.1 lb ae/ac to as much as about 16 lb ae/ac over a growing season (for example, dicamba could be applied at a rate of about 0.5 lb ae/acre to about 2.0 lb ae/acre). An herbicidally effective amount of glutamine synthetase inhibitors for use in the area for controlling weeds should consist of a range from about 0.1 lb ae/acre to as much as about 10 lb ae/acre over a growing season (for example, glufosinate could be applied at a rate of about 0.4 lb ai/acre to about 1.59 lb ai/acre). An herbicidally effective amount of EPSPS inhibitors for use in the area for controlling weeds should consist of a range from about 0.5 lb ae/ac to about 12 lb ae/ac over a growing season (for example, glyphosate could be applied at a rate of about 0.75 lb ae/acre to about 2.25 lb ae/acre).

The invention provides methods for controlling volunteer maize comprising maize event MON87429 in an area for crop cultivation by applying an herbicidally effective amount of at least one cyclohexanedione (DIM) herbicide, such as clethodim, sethoxydim, and tralkoxydim, where the herbicide application prevents growth of maize comprising maize event MON87429. An herbicidally effective amount of a DIM herbicide for use in the area for controlling volunteer maize could be applied at a rate of about 0.03 lb ai/acre to about 2.75 lb ai/acre over a growing season (for example, clethodim could be applied from about 0.0625 lb ai/acre to about 0.125 lb ai/acre and sethoxydim could be applied from about 0.188 lb ai/acre to 0.281 about lb ai/acre).

Methods for producing plants and seeds containing maize event MON87429 are provided. Plants may be bred using any method known in the art, for example, descriptions of breeding methods that are commonly used can be found in W R Fehr, in *Breeding Methods for Cultivar Development*, Wilcox J. ed., American Society of Agronomy, Madison Wis. (1987). Plants may be self-pollinated (also known as "selfing") or cross-pollinated (also known as "crossing"). Plants containing maize event MON87429 may be self-pollinated to generate a true breeding line of plants that are homozygous for maize event MON87429. Selfing results in progeny known as "inbred" and can be used to produce inbred lines that are genetically uniform. Alternatively, plants containing maize event MON87429 may be cross-pollinated (bred with another plant that is transgenic or nontransgenic) to produce a varietal or a hybrid seed. Seed and progeny plants made by the methods of the invention contain maize event MON87429. Application of one or more herbicide for which maize event MON87429 confers tolerance may be used to select progeny that contain maize event MON87429. Alternatively, progeny may be analyzed using diagnostic methods to select for plants or seeds containing maize event MON87429. Progeny may be varietal or hybrid plants; may be grown from seeds produced by a plant containing maize event MON87429 or from seeds produced by a plant fertilized with pollen from a plant containing maize event MON87429; and may be homozygous or heterozygous for maize event MON87429.

Methods for producing hybrid seed using maize event MON87429 are provided. Plants comprising maize event MON87429 have expression of the glyphosate tolerant protein CP4-EPSPS in all tissues except male reproductive tissues. This results in glyphosate tolerance in vegetative and female reproductive tissues and glyphosate sensitivity in male reproductive tissues. This glyphosate sensitivity can be used to induce male-sterility through the proper application of glyphosate. Glyphosate is a systemic herbicide that is translocated from source to sink tissues in plants. Due to the rate of glyphosate metabolism in maize, application to plants comprising maize event MON87429 prior to the development of the male reproductive tissue may prevent pollen development, pollen shed, or anther extrusion. This glyphosate-induced male-sterility can be used to increase the efficiency of hybrid seed production, for example by eliminating or reducing the need to physically emasculate the maize plant used as a female in a given cross during hybrid seed production.

The invention provides a method of producing hybrid seed comprising (a) growing a plant comprising maize event MON87429, (b) applying an effective amount of glyphosate to the plant to induce male-sterility, wherein the herbicide application is prior to or during the development of the male reproductive tissue of the plant thereby inducing male-sterility in the plant; (c) fertilizing the plant with pollen from a second plant; and (d) harvesting hybrid seed from the plant. In one embodiment, the glyphosate is applied prior to or during the development at an effective amount of about 0.25 lb ae/acre to about 11.0 lb ae/acre total, applied in one or more application. In another embodiment, the step of fertilizing may be accomplished by allowing passive fertilization (for example through wind pollination), by other means such as mechanical or hand pollination, or by a combination of these. The herbicide application may be applied in one or more application prior to or during the development of the male reproductive tissue, such as at a stage selected from the group consisting of the V4, V5, V6, V7, V8, V9, V10, V11, V12, V13, and V14 stage of maize plant development and may prevent at least pollen development, pollen shed, or anther extrusion. The male-sterility may be partial or complete. In one embodiment, the effective amount of glyphosate would be about 0.5 lb ae/acre to about 2.5 lb ae/acre total (in one application or split into two or more applications) applied at the V4 through V8 stage or up to 100 growing degree units (GDU) before flowering.

Plants, progeny, seeds, cells, and plant parts of the invention may also contain one or more additional maize trait(s) or transgenic events, particularly those introduced by crossing a maize plant containing maize event MON87429 with another maize plant containing the additional trait(s) or transgenic events. Such trait(s) or transgenic events include, but are not limited to, increased insect resistance, increased water use efficiency, increased yield performance, increased drought resistance, increased seed quality, improved nutritional quality, hybrid seed production, and herbicide tolerance, in which the trait is measured with respect to a maize plant lacking such transgenic trait. Maize transgenic events are known to one of skill in the art; for example, a list of such traits is provided by the United States Department of Agriculture's (USDA) Animal and Plant Health Inspection Service (APHIS) and can be found on their website at www.aphis.usda.gov. Two or more transgenic events may thus be combined in a progeny seed or plant by crossing two parent plants each comprising one or more transgenic event(s), collecting progeny seed, and selecting for progeny seed or plants that contain the two or more transgenic events; these steps may then be repeated until the desired combination of transgenic events in a progeny is achieved. Back-crossing to a parental plant and out-crossing with a non-transgenic plant are also contemplated, as is vegetative propagation.

A deposit of a representative sample of at least 625 seeds comprising maize event MON87429 has been made according to the Budapest Treaty with the American Type Culture Collection (ATCC®) having an address at 10801 University Boulevard, Manassas, Va. USA, Zip Code 20110. The ATCC Patent Deposit Designation (accession number) for seeds comprising maize event MON87429 is PTA-124635 and the date of deposit was Jan. 12, 2018. The deposit has been accepted under the Budapest Treaty and will be maintained in the depository for a period of 30 years, or 5 years after the last request, or for the effective life of the patent, whichever is longer.

As used herein, the term "comprising" means "including but not limited to".

EXAMPLES

The following examples are included to more fully describe the invention. Summarized are the construction and testing of thirty-five expression constructs, the production of over fifteen thousand unique events, and the analysis of hundreds of thousands of individual plants over seven years through the rigorous molecular, agronomic, and field testing required for the creation and ultimate selection of maize event MON87429.

It should be appreciated by those of skill in the art that many modifications can be made in the specific examples which are disclosed and still obtain a similar result. Certain agents which are both chemically and physiologically related may be substituted for the agents described herein while achieving the same or similar results. All such substitutions and modifications apparent to those skilled in the art are deemed to be within the scope of the invention.

Example 1: Expression Cassette Testing, Construct Design, and R0 Plant Testing

This example describes the design and testing in maize plants of thirty-five different constructs. Each construct contained four expression cassettes, each expression cassette used for expressing a different transgene. This testing was done to select the best construct to use for expressing all four transgenes in maize. Each construct had a unique configuration, varying by expression cassette orientation and expression elements.

Various individual expression cassettes with different expression element combinations and transgenes were designed, cloned into plant transformation vectors, and tested for trait efficacy in maize plants to create a pool of the best individual expression cassettes. Using this pool of individual expression cassettes, 35 different constructs were designed so that each contained four expression cassettes (each expression cassette having the transgene for PAT, DMO, CP4-EPSPS, or FT) and could be used to test the four-way combination of the different expression cassettes. The expression cassette combinations varied by expression elements, protein coding sequence, and orientation. This resulted in the testing of two PAT expression cassettes, 6 DMO expression cassettes, 5 FT expression cassettes, 18 CP4-EPSPS expression cassettes.

The 35 four-expression cassette constructs were cloned into plant transformation vectors, and these vectors were used for Agrobacterium-mediated transformation of LH244 maize immature embryos using methods known in the art to produce 15,326 unique transformation events, each made by a random insertion of the transgene insert into the maize genome. R0 plants were then regenerated from the transgenic cells, and rooted plants with normal phenotypic characteristics were transferred to soil for growth and further assessment.

The 15,326 R0 plants were analyzed for having a single copy of the transgenic insert and absence of vector backbone sequence. Plants with a single copy of the insert were advanced for herbicide tolerance efficacy testing. Single copy R0 plants were assessed in the greenhouse for tolerance to quizalofop (0.16 lb ai/ac of Assure II® herbicide) followed by a tank mix of glufosinate (0.98 lb ae/ac of Ignite® 280 herbicide), dicamba (2.0 lb ae/ac of Clarity® herbicide), or 2,4-D (2.0 lb ae/ac 2,4-D Amine 4® herbicide)

(or a combination of any of these) sprayed at the V1/V2 growth stage. Plants that showed >30% injury were discarded.

From the initial 15,326 unique transformation events produced using the 35 transformation vectors, 1,945 unique events were selected after analyzing the copy number and herbicide spray data. Data are provided in Table 2. The R0 plants for the selected events were self-pollinated to produce R1 seed or crossed to produce F1 seed that was advanced to first season field trials.

TABLE 2

First Season Field Trial Inbred Efficacy

| Construct | R0 Events | Events Advanced |
|---|---|---|
| HT4-1 | 515 | 39 |
| HT4-2 | 263 | 30 |
| HT4-3 | 158 | 53 |
| HT4-4 | 340 | 79 |
| HT4-5 | 97 | 20 |
| HT4-6 | 121 | 24 |
| HT4-7 | 49 | 10 |
| HT4-8 | 88 | 16 |
| HT4-9 | 853 | 112 |
| HT4-10 | 366 | 55 |
| HT4-11 | 600 | 78 |
| HT4-12 | 729 | 73 |
| HT4-13 | 459 | 63 |
| HT4-14 | 1026 | 151 |
| HT4-15 | 224 | 44 |
| HT4-16 | 1877 | 76 |
| HT4-17 | 365 | 39 |
| HT4-18 | 127 | 24 |
| HT4-19 | 94 | 27 |
| HT4-20 | 23 | 4 |
| HT4-21 | 409 | 74 |
| HT4-25 | 123 | 13 |
| HT4-26 | 57 | 3 |
| HT4-27 | 76 | 1 |
| HT4-29 | 118 | 5 |
| HT4-30 | 177 | 24 |
| HT4-31 | 311 | 18 |
| HT4-32 | 913 | 123 |
| HT4-34 | 884 | 124 |
| HT4-36 | 1364 | 185 |
| HT4-37 | 1019 | 179 |
| HT4-38 | 1021 | 129 |
| HT4-39 | 98 | 15 |
| HT4-50 | 250 | 26 |
| HT4-51 | 132 | 9 |
| Total | 15326 | 1945 |

Example 2: First Season Field Trials

Field trials were conducted over many years with events advanced from the R0 analysis for each of the 35 constructs, and the performance of every plant for each construct in their first season of field trials was then analyzed as a set. Each construct was thus represented by many unique events. This allowed a larger number of constructs to be tested in first season field trials while only advancing beyond the first season trial the top performing constructs. Separate first season field trials were conducted with R2 plants (homozygous for each event) for (1) inbred efficacy for glufosinate+dicamba, quizalofop, and 2,4-D tolerance, (2) Roundup Hybridization System (RHS) efficacy, and (3) herbicide pressure testing for tolerance to higher application rates of herbicides quizalofop, 2,4-D, glufosinate, and dicamba.

An inbred efficacy screen of plants to evaluate herbicide tolerance for glufosinate+dicamba, quizalofop, and 2,4-D was carried out. Herbicide treatments consisted of: a tank-mix application of glufosinate at 0.8 lb ai/acre plus dicamba at 2.0 lb ae/acre; quizalofop at 0.16 lb ai/acre; or 2,4-D at 2.0 lb ai/acre. Plots were visually rated for crop injury 10-14 days after herbicide treatment on a scale of 0-100 with "0" being no crop injury and "100" being complete crop destruction. Plant height (PHT), ear height (EHT), days to 50% silk (S50D), days to 50% pollen (P50D), shell weight (SHW), test weight (TWT), moisture (MST), and grain yield (YLD) were also collected. All data were subjected to analysis of variance and means separation at $p<0.05$. Overall averages for multiple plants containing the same event were used, and inbred efficacy was summarized for glufosinate+dicamba, quizalofop, and 2,4-D as excellent (4), good (3), fair (2), or poor (1) or not applicable (NA). Data are provided in Table 3.

TABLE 3

First Season Field Trial Inbred Efficacy

| Construct | Glufosinate/Dicamba | Quizalofop | 2,4-D |
|---|---|---|---|
| HT4-1 | 4 | 4 | 4 |
| HT4-2 | 4 | 4 | 4 |
| HT4-3 | 4 | 4 | 4 |
| HT4-4 | 4 | 4 | 4 |
| HT4-5 | 4 | 4 | 4 |
| HT4-6 | 4 | 4 | 4 |
| HT4-7 | 4 | 4 | 4 |
| HT4-8 | 4 | 4 | 4 |
| HT4-9 | 4 | 4 | 4 |
| HT4-10 | 4 | 4 | 4 |
| HT4-11 | 4 | 4 | 4 |
| HT4-12 | 4 | 4 | 4 |
| HT4-13 | 4 | 4 | 4 |
| HT4-14 | 4 | 4 | 4 |
| HT4-15 | 4 | 4 | 4 |
| HT4-16 | 4 | 4 | 4 |
| HT4-17 | 4 | 4 | 4 |
| HT4-18 | 4 | 4 | 3 |
| HT4-19 | 4 | 4 | 4 |
| HT4-20 | 4 | 4 | 4 |
| HT4-21 | 4 | 4 | 4 |
| HT4-25 | 4 | 4 | 4 |
| HT4-26 | NA | NA | NA |
| HT4-27 | NA | NA | NA |
| HT4-29 | 4 | 4 | 4 |
| HT4-30 | 4 | 4 | 4 |
| HT4-31 | 4 | 4 | 4 |
| HT4-32 | 4 | 4 | 4 |
| HT4-34 | 4 | 4 | 4 |
| HT4-36 | 4 | 4 | 4 |
| HT4-37 | 4 | 4 | 4 |
| HT4-38 | 4 | 4 | 4 |
| HT4-39 | 4 | 4 | 4 |
| HT4-50 | 4 | 4 | 4 |
| HT4-51 | 4 | 4 | 4 |

An RHS efficacy screen of plants was carried out to identify differences in glyphosate tolerance and glyphosate-induced tassel sterility of inbred material. A single herbicide treatment was used for screening and consisted of glyphosate at 1.5 lb ae/acre applied to V2 followed by 0.75 lb ae/acre to approximately V8 (875 growing degree days) followed by approximately V10 (1025 growing degree days). Plots were visually rated for % crop injury (CIPV2, CIPV8, CIPV10, and CIPVT) 10-14 days after herbicide application on a scale of 0 to 100 plus a final injury rating at VT (after tassel emergence). Plots were also visually rated for % silk emergence [(SES9A (S90) and SES9C (S90 plus 4 days) SES9E (S90 plus 8 days)] and % anther extrusion [(AES9A (S90), AES9C (S90 plus 4 days), and AES9E (S90 plus 8 days)] on a similar scale of 0 to 100 with "0" being no silk emergence or anther extrusion and "100" being complete silk emergence or anther extrusion. Other agronomic parameters were collected, as in the inbred efficacy screen. Overall averages for multiple plants containing the same event were used, and glyphosate tolerance, tassel sterility, and yield were each summarized as excellent (4), good (3), fair (2), or poor (1) or not applicable (NA). Data are provided in Table 4.

TABLE 4

First Season Field Trial RHS Efficacy

| Construct | Glyphosate Tolerance | Tassel Sterility | Yield |
|---|---|---|---|
| HT4-1 | 4 | 2 | NA |
| HT4-2 | 4 | 2 | NA |
| HT4-3 | 2 | 2 | NA |
| HT4-4 | 4 | 2 | NA |
| HT4-5 | 2 | 2 | NA |
| HT4-6 | 2 | 2 | NA |
| HT4-7 | 4 | 2 | NA |
| HT4-8 | 4 | 2 | NA |
| HT4-9 | 2 | 2 | NA |
| HT4-10 | 2 | 2 | NA |
| HT4-11 | 2 | 2 | NA |
| HT4-12 | 4 | 2 | NA |
| HT4-13 | 4 | 2 | NA |
| HT4-14 | 4 | 4 | 4 |
| HT4-15 | 4 | 2 | NA |
| HT4-16 | 3/2 | 4 | 1 |
| HT4-17 | 4 | 2 | NA |
| HT4-18 | 2 | 2 | NA |
| HT4-19 | 1 | NA | NA |
| HT4-20 | 1 | NA | NA |
| HT4-21 | 4 | 2 | NA |
| HT4-25 | 2 | 2 | NA |
| HT4-26 | NA | NA | NA |
| HT4-27 | NA | NA | NA |
| HT4-29 | 1 | NA | NA |
| HT4-30 | 4 | 2 | NA |
| HT4-31 | 2 | 2 | NA |
| HT4-32 | 4 | 4 | 4 |
| HT4-34 | 4 | 4 | 4 |
| HT4-36 | 4 | 2 | NA |
| HT4-37 | 4 | 2 | NA |
| HT4-38 | 4 | 2 | NA |
| HT4-39 | 4 | 2 | NA |
| HT4-50 | 2 | 2 | NA |
| HT4-51 | 2 | 2 | NA |

An herbicide pressure test was conducted to evaluate construct level crop tolerance to higher application rates of herbicides quizalofop, 2,4-D, glufosinate, and dicamba as follows. Quizalofop treatments consisted of: 1) quizalofop at 0.32 lb ai/acre (4×) plus 0.25% v/v non-ionic surfactant (NIS) applied to VE-V2 followed by V4 followed by V8; 2) quizalofop at 0.64 lb ai/acre (8×) plus 0.25% v/v NIS applied to VE-V2 followed by V4 followed by V8; or 3) quizalofop at 1.28 lb ai/acre (16×) plus 0.25% v/v NIS applied to VE-V2 followed by V4 followed by V8. 2,4-D treatments consisted of 1) 2,4-D amine at 2 lb ai/acre plus 0.25% v/v non-ionic surfactant (NIS) applied to VE-V2 followed by V4 followed by V8; 2) 2,4-D amine at 4 lb ai/acre plus 0.25% v/v NIS applied to VE-V2 followed by V4 followed by V8; 3) 2,4-D amine at 8 lb ai/acre plus 0.25% v/v NIS applied to VE-V2 followed by V4 followed by V8; or 4) 2,4-D amine at 16 lb ai/acre plus 0.25% v/v NIS applied to VE-V2 followed by V4 followed by V8. Glufosinate treatments consisted of: 1) glufosinate 1.0 lb ai/acre applied to V2 followed by V4 followed by V8; 2) glufosinate 2.0 lb ai/acre applied to V2 followed by V4 followed by V8; 3) glufosinate 4.0 lb ai/acre applied to V2 followed by V4 followed by V8; or 4) glufosinate 8.0 lb ai/acre applied to V2 followed by V4 followed by V8. Dicamba treatments consisted of: 1) dicamba at 2.0 lb applied to V2 followed by V4 followed by V8; 2) dicamba at 4.0 lb applied to V2 followed by V4 followed by V8; or 3) dicamba at 8.0 lb applied to V2 followed by V4 followed by V8. 4) dicamba at 16 lb applied to V2 followed by V4 followed by V8. Plots were rated visually for crop injury and agronomic parameters were collected, as in the inbred efficacy screen. Overall averages for multiple plants containing the same event were used, and herbicide tolerance efficacy was summarized for each of the four herbicides as excellent (4), good (3), fair (2), or poor (1) or not applicable (NA). Data are provided in Table 5.

TABLE 5

First Season Field Trial Herbicide Pressure Test

| Construct | Glufosinate | Dicamba | Quizalofop | 2,4-D |
|---|---|---|---|---|
| HT4-1 | 4 | 4 | 3 | 3 |
| HT4-2 | 4 | 4 | 4 | 4 |
| HT4-3 | 4 | 4 | 4 | 4 |
| HT4-4 | 4 | 4 | 4 | 4 |
| HT4-5 | 4 | 4 | 4 | 4 |
| HT4-6 | 4 | 4 | 4 | 4 |
| HT4-7 | 4 | 4 | 4 | 4 |
| HT4-8 | 4 | 4 | 4 | 4 |
| HT4-9 | 4 | 4 | 4 | 4 |
| HT4-10 | 4 | 4 | 4 | 4 |
| HT4-11 | 4 | 4 | 4 | 4 |
| HT4-12 | 4 | 4 | 4 | 4 |
| HT4-13 | 4 | 4 | 4 | 4 |
| HT4-14 | 4 | 4 | 4 | 4 |
| HT4-15 | 4 | 4 | 4 | 4 |
| HT4-16 | 4 | 4 | 4 | 4 |
| HT4-17 | 4 | 4 | 4 | 4 |
| HT4-18 | 4 | 4 | 4 | 4 |
| HT4-19 | 4 | 4 | 4 | 4 |
| HT4-20 | 4 | 4 | 4 | 4 |
| HT4-21 | 4 | 4 | 4 | 4 |
| HT4-25 | 4 | 4 | 4 | 4 |
| HT4-26 | NA | NA | NA | NA |
| HT4-27 | NA | NA | NA | NA |
| HT4-29 | 4 | 4 | 4 | 4 |
| HT4-30 | 4 | 4 | 4 | 4 |
| HT4-31 | 4 | 4 | 4 | 4 |
| HT4-32 | 4 | 4 | 4 | 4 |
| HT4-34 | 4 | 4 | 4 | 4 |
| HT4-36 | 4 | 4 | 4 | 4 |
| HT4-37 | 4 | 4 | 4 | 4 |
| HT4-38 | 4 | 4 | 4 | 4 |
| HT4-39 | 4 | 4 | 4 | 4 |
| HT4-50 | 4 | 4 | 4 | 4 |
| HT4-51 | 4 | 4 | 4 | 4 |

The data of the composite performance of R2 plants produced with each of 35 constructs was compiled and analyzed for (1) the inbred efficacy test for glufosinate+dicamba, quizalofop, and 2,4-D tolerance, (2) the RHS efficacy test for glyphosate tolerance, tassel sterility, and yield, and (3) the herbicide pressure testing for tolerance to higher application rates of herbicides quizalofop, 2,4-D, glufosinate, and dicamba. Using this data, 3 constructs (HT4-14, HT4-32, and HT4-34) were selected for advancement from the 35 constructs tested. Events for these 3 constructs were then advanced to second season field trials.

Example 3: Molecular Analysis

Molecular analysis was conducted concurrently with the field trials on events that were advanced. DNA amplification and sequencing were used to confirm the insert sequence, insert copy number, and absence of backbone in the insert. The insertion site in the maize genome for each event was mapped. Northern analysis was done to detect and measure mRNA transcripts of the pat, dmo, ft_t, and cp4-epsps genes. N-terminal protein sequencing of the PAT, DMO, FT_T, and CP4-EPSPS proteins purified from transgenic plants was done to confirm the recombinant protein sequence. Western blot analysis to detect the PAT, DMO, FT_T, and CP4-EPSPS proteins was done with transgenic plant samples. In depth Southern analysis was performed on genomic DNA from R1 plants to confirm copy number and the absence of backbone.

Example 4: Advanced Field Trials

Advanced field trials (second season testing and beyond) were conducted over many years with events advanced from the first season field trials for constructs HT4-14, HT4-32, and HT4-34. The performance of many individual plants for each event in each field trial was analyzed as a set. Each event was thus represented by many unique plants. This allowed the performance of each event to be analyzed under many conditions, in different locations and geographies, and for a variety of properties.

Field trials were conducted with inbred plants (homozygous for the event) and hybrid plants (hemizygous for the event) to assess (1) trait efficacy for commercial rates of glufosinate, dicamba, quizalofop, and 2,4-D tolerance, (2) agronomic performance, (3) Roundup Hybridization System (RHS) efficacy and glyphosate, and (4) herbicide pressure testing for tolerance to higher application rates of quizalofop, 2,4-D, glufosinate, and dicamba herbicides.

In the Field Season 1 trials, 30 events were tested for construct HT4-14, 41 events were tested for construct HT4-32, and 21 events were tested for construct HT4-34. Using the composite data from these trials, events were selected for advancement. In the Field Season 2 trials, 15 events were tested for the HT4-14 construct, 38 events for the HT4-32 construct, and 38 events for the HT4-34 construct (this number included some events not tested in Field Season 1 due to because of seed shortages during that season). Events for construct HT4-14 were characterized by molecular analysis as described in Example 3 and this data was also used to select events. The composite data from these trials and the in depth molecular characterization of events for the HT4-14 construct was used to select 3 events for advancement for the HT4-14 construct. The composite data from these trials was used to select 24 events for advancement for the HT4-32 construct and to decide not to advance any events for the HT4-34 construct. In the Field Season 3 trials, the 3 events for construct HT4-14 and 24 events for the HT4-34 construct were tested. The composite data from these trials was used to select 2 events for advancement for the HT4-14 construct and to decide not to advance any events for the HT4-32. The Field Season 4 trials were used to compare the final two events in a large number of locations, under a variety of conditions, and in hybrid and inbred germplasm in order to produce the data necessary to select the superior event. Table 6 provides the number of unique events tested for each construct in the field trials conducted during each season.

TABLE 6

Advanced Field Trials Summary

| Milestone | HT4-14 | HT4-32 | HT4-34 |
|---|---|---|---|
| Field Season 1 | 30 | 41 | 21 |
| Field Season 2 | 15 | 38 | 38 |

TABLE 6-continued

Advanced Field Trials Summary

| Milestone | HT4-14 | HT4-32 | HT4-34 |
|---|---|---|---|
| Field Season 3 | 3 | 24 | 0 |
| Field Season 4 | 2 | 0 | 0 |
| Final event selection | 1 | 0 | 0 |

The agronomic performance field trials were run during the same season as the trait efficacy field trials. All field trials used a randomized complete block design and were conducted at multiple locations. Field trials were conducted at locations in North America and South America. For both efficacy and agronomic field trials, agronomic scoring was collected throughout the field trial season, and at the end of the season yield was determined (efficacy yield or agronomic yield). Efficacy field trials were conducted to assess crop injury 10 to 14 days following herbicide application. The target crop injury rating was a score of less than 10% for advancement of an event. For agronomic field trials, the plots were maintained weed free and none of the test herbicides were applied during the growing season. The hybrid agronomic field trials included controls of a comparable hybrid (hybrid control) produced using the same parental maize lines used to make the transgenic hybrid cross, but not containing a transgenic event. Inbred controls were a comparable inbred to the transgenic inbred lines.

To compare the field trial data, meta-analysis was performed using the aggregate of all plants in the multi-season, multi-location field trial data. As an example, Table 7 illustrates over multiple seasons the number of replications (reps) for which an observation was repeated for two selected HT4-14 events and the total number of individual plants tested in each trial for each event.

TABLE 7

Field trial replications

| Milestone | Event | Total Reps | Total Plants |
|---|---|---|---|
| Field Season 1 | EVENT 2 | 235 | 16,450 |
| Field Season 1 | MON87429 | 235 | 16,450 |
| Field Season 2 | EVENT 2 | 100 | 7,000 |
| Field Season 2 | MON87429 | 100 | 7,000 |
| Field Season 3 | EVENT 2 | 529 | 37,030 |
| Field Season 3 | MON87429 | 513 | 35,910 |
| Field Season 4 | EVENT 2 | 228 | 15,960 |
| Field Season 4 | MON87429 | 228 | 15,960 |
| Field Season 4 | EVENT 2 | 56 | 3,920 |
| Field Season 4 | MON87429 | 2465 | 172,550 |

Meta-analysis of the multiple hybrid efficacy field trials was completed for comparison of the hybrid injury ratings. As an example, Table 8 provides the injury rating over multiple seasons for two selected HT4-14 events scored at V8 (where V8 analysis encompasses the cumulative injury from V2, V4, V6, and V8 herbicide applications) with a statistical least significant difference at 95% confidence level (LSD at $p<0.05$). Plants containing maize event MON87429 and plants containing Event 2 both performed well in these trials.

TABLE 8

Meta-analysis of injury rating from hybrid efficacy field trials

| Milestone | Event | V8 injury | LSD (P < 0.05) |
|---|---|---|---|
| Field Season 1 | MON87429 | 1.3 | 2.1 |
| Field Season 1 | EVENT 2 | 1.1 | 2.1 |
| Field Season 2 | MON87429 | 1.7 | 3.1 |
| Field Season 2 | EVENT 2 | 2.6 | 3.1 |
| Field Season 3 | MON87429 | 0.08 | 3.4 |
| Field Season 3 | EVENT 2 | 0.13 | 3.4 |

Meta-analysis of the multiple hybrid efficacy field trials was completed for comparison of yield as bushels/acre (Bu/ac). As an example, Table 9 provides yield from hybrids over multiple seasons for two selected HT4-14 events with a statistical least significant difference at 95% confidence level (LSD at p<0.05). Plants containing maize event MON87429 and plants containing Event 2 both performed well in these trials.

TABLE 9

Meta-analysis of yield from hybrid efficacy field trials

| Milestone | Event | Yield (Bu/ac) | LSD (p < 0.05) |
|---|---|---|---|
| Field Season 1 | MON87429 | 222 | 12 |
| Field Season 1 | EVENT 2 | 222 | 12 |
| Field Season 2 | MON87429 | 197 | 15.4 |
| Field Season 2 | EVENT 2 | 197 | 15.4 |
| Field Season 3 | MON87429 | 210.9 | 9.1 |
| Field Season 3 | EVENT 2 | 211.5 | 9.1 |

Pressure testing field trials with herbicide applied at higher application rates than commercial use were conducted with hybrid and inbred plants containing a single transgenic event. The herbicides glufosinate (over the range of 1.6 to 6.4 lb ai/acre), dicamba (over the range of 2.0 to 16 lb ai/acre), quizalofop (over the range of 0.32 to 1.28 lb ai/acre), 2,4-D (over the range of 2.0 to 8.0 lb ai/acre), and glyphosate (at 3.0 lb ae/acre) were applied in field trials for pressure testing of the efficacy of the herbicide tolerance traits. At the end of the season, the hybrid pressure testing field trials were harvested and yield (Bu/ac) was determined. As an example, Table 10 provides yield data from hybrids and inbreds in different trials for two selected HT4-14 events with a statistical least significant difference at 95% confidence level (LSD at p<0.05). Plants containing maize event MON87429 and plants containing Event 2 both performed well in hybrid and inbred yield trials for all of the herbicide treatments. The results suggested that further field testing could identify an inbred yield advantage for maize event MON87429 over Event 2.

TABLE 10

Yield from hybrid/inbred pressure testing efficacy field trials

| Herbicide | Plant | Event | Yield (Bu/ac) | LSD (p < 0.05) |
|---|---|---|---|---|
| Glufosinate | Hybrid | MON87429 | 256 | 28.4 |
| Glufosinate | Hybrid | EVENT 2 | 240 | 28.4 |
| Dicamba | Hybrid | MON87429 | 264 | 39.2 |
| Dicamba | Hybrid | EVENT 2 | 256 | 39.2 |
| Quizalofop | Hybrid | MON87429 | 251 | 48.5 |
| Quizalofop | Hybrid | EVENT 2 | 257 | 48.5 |
| 2,4-D | Hybrid | MON87429 | 261 | 38.4 |
| 2,4-D | Hybrid | EVENT 2 | 254 | 38.4 |
| Glyphosate | Inbred | MON87429 | 90.1 | 46 |
| Glyphosate | Inbred | EVENT 2 | 67.2 | 46 |

Hybrid agronomic field trials were conducted, agronomic measures were collected throughout the season, and agronomic yield was determined at the end of the season. Meta-analysis across the multi-season, multi-location hybrid agronomic field trials was used to compare the yield of the hybrid control and the hybrids. As an example, Table 11 provides yield data (Bu/ac) for two selected HT4-14 events with a statistical least significant difference at 95% confidence level (LSD at p<0.05). Plants containing maize event MON87429 and plants containing Event 2 both performed well in these trials, and no statistical difference in hybrid yield was found for plants containing either of these events when compared to the control plants.

TABLE 11

Meta-analysis of yield from hybrid agronomic field trials

| Milestone | Event | Yield (Bu/ac) | LSD (p < 0.05) |
|---|---|---|---|
| Field Season 1 | Control - none | 222 | 9 |
| Field Season 1 | MON87429 | 220 | 9 |
| Field Season 1 | EVENT 2 | 224 | 9 |
| Field Season 2 | Control - none | 224.6 | 13.7 |
| Field Season 2 | MON87429 | 211 | 13.7 |
| Field Season 2 | EVENT 2 | 215 | 13.7 |
| Field Season 3 | Control - none | 213.6 | 9.7 |
| Field Season 3 | MON87429 | 213.3 | 9.7 |
| Field Season 3 | EVENT 2 | 212.4 | 9.7 |

Inbred efficacy field trials were conducted for glyphosate tolerance and the Roundup Hybridization System (RHS) and yield was determined at the end of the season. Glyphosate was applied at a rate of 1.5 lb ae/acre for weed control followed by two sterility applications of glyphosate at 0.75 lb ae/acre at approximately V8 followed by 0.75 lb ae/acre at approximately V10. Meta-analysis across the multi-season, multi-location inbred efficacy field trials was used to compare the yield of plants. As an example, Table 12 provides yield data (Bu/ac) for two selected HT4-14 events with a statistical least significant difference at 95% confidence level (LSD at p<0.05). Field Season 2 and Field Season 3 trials both showed a statistically significant decrease in yield in plants containing Event 2 when compared to plants containing the Event MON87429. These data indicated the superior performance in inbred efficacy yield trials of plants containing maize event MON87429.

TABLE 12

Meta-analysis of yield from glyphosate treated inbred efficacy field trials

| Milestone | Event | Yield (Bu/ac) | LSD (p < 0.05) |
|---|---|---|---|
| Field Season 1 | MON87429 | 89.9 | 14.3 |
| Field Season 1 | EVENT 2 | 87.5 | 14.3 |
| Field Season 2 | MON87429 | 119.6 | 18.0 |
| Field Season 2 | EVENT 2 | 99.0 | 18.0 |

TABLE 12-continued

Meta-analysis of yield from glyphosate treated inbred efficacy field trials

| Milestone | Event | Yield (Bu/ac) | LSD (p < 0.05) |
|---|---|---|---|
| Field Season 3 | MON87429 | 105.6 | 10.5 |
| Field Season 3 | EVENT 2 | 90.13 | 10.5 |

Inbred agronomic field trials were conducted and yield was determined at the end of the season for untreated plants. The trials included controls of inbred lines comparable to the transgenic inbred lines. Meta-analysis across the multi-season, multi-location inbred agronomic field trials was conducted comparing yield for the paired control and the transgenic inbreds. As an example, Table 13 provides yield data (Bu/ac) for two selected HT4-14 events with a statistical least significant difference at 95% confidence level (LSD at $p<0.05$). No statistical difference in inbred agronomic yield was found between the control plants and plants containing maize event MON87429. In contrast, for Field Season 3 trials, there was a statistically significant decrease in yield in plants containing Event 2 when compared to control plants and plants containing maize event MON87429. These data indicated the superior performance in inbred agronomic yield trials of plants containing maize event MON87429.

TABLE 13

Meta-analysis of yield from inbred agronomic field trials

| Milestone | Event | Total (Bu/ac) | LSD (p < 0.05) |
|---|---|---|---|
| Field Season 1 | Control - none | 105.2 | 8.9 |
| Field Season 1 | MON87429 | 104.1 | 8.9 |
| Field Season 1 | EVENT 2 | 102.5 | 8.9 |
| Field Season 2 | Control - none | 103.7 | 15.3 |
| Field Season 2 | MON87429 | 93.4 | 15.3 |
| Field Season 2 | EVENT 2 | 91.4 | 15.3 |
| Field Season 3 | Control - none | 116.6 | 6.2 |
| Field Season 3 | MON87429 | 112.8 | 6.2 |
| Field Season 3 | EVENT 2 | 106.1 | 6.2 |

Hybrid efficacy trials were conducted at four locations in Argentina to evaluate plant tolerance to glufosinate, dicamba, quizalofop, haloxyfop, 2,4-D, and glyphosate. Plants containing MON87429 were crossed with plants containing both maize event MON88017 and maize event MON89034 to produce progeny containing all three events (MON87429×MON88017×MON89034). Herbicide treatments consisted of 1) a non-treated control; 2) glufosinate at 0.448 kg ai/ha applied at the V2 stage followed by the same application to the V6 stage; 3) glufosinate at 0.896 kg ai/ha applied at the V2 stage followed by the same application to the V6 stage; 4) dicamba at 0.56 lb ae/acre applied at the V2 stage followed by the same application to the V6 stage; 5) dicamba at 1.12 lb ae/acre applied at the V2 stage followed by the same application to the V6 stage; 6) quizalofop at 0.09 kg ae/ha applied at the V2 stage followed by the same application to the V6 stage; 7) quizalofop at 0.18 kg ae/ha applied at the V2 stage followed by the same application to the V6 stage; 8) haloxyfop at 0.1 kg ae/ha applied at the V2 stage followed by the same application to the V6 stage; 9) haloxyfop at 0.2 kg ae/ha applied at the V2 stage followed by the same application to the V6 stage; 10) 2,4-D at 1.12 lb ai/acre applied at the V2 stage followed by the same application to the V6 stage; 11) 2,4-D at 2.24 lb ae/acre applied at the V2 stage followed by the same application to the V6 stage; or 12) glyphosate at 2.24 lb ae/acre applied at the V2 stage followed by the same application to the V6 stage. Data collection consisted of crop injury 10 to 14 days after V2 and V6 herbicide applications and a final rating at VT, days to 50% pollen, days to 50% silk, plant height, ear height, shell weight, test weight, moisture, and grain yield. All data were subjected to analysis of variance and means separated at $p<0.05$.

Herbicide tolerance of plants containing MON87429×MON88017×MON89034 was excellent (<10% crop injury) over all rates of glyphosate, glufosinate, dicamba, quizalofop, haloxyfop, and 2,4-D tested. Herbicide treatment rates did not produce differences with respect to visual crop injury. Ear height was not significantly different for any of the treatments compared to the standard herbicide treatment 12 (glyphosate at 2.24 lb ae/acre). There was no significant reduction in plant height or test weight, increase in grain moisture, delay in maturity (measured as increase days to 50% pollen or silk), decrease in grain yield of the plants containing MON87429×MON88017×MON89034 within any treatment over that of non-treated plants. Hybrid plants produced through the cross of a plant containing MON87429 with a plant containing an event providing glyphosate tolerance in male tissues (such as commercially available maize events MON88017 or NK603) provide excellent vegetative tolerance to glyphosate, glufosinate, dicamba, quizalofop, haloxyfop, and 2,4-D when applied at commercial label rates.

Three years of field trials were used to test for control of plants comprising maize event MON87429 using clethodim. These trials assessed the use in volunteer control methods of a DIM herbicide with plants containing maize event MON87429. Plants were treated with clethodim at commercial label rates and complete control of plants comprising maize event MON87429 was observed.

The data accumulated from the molecular analysis and from the field trials with inbred and hybrid plants assessing (1) trait efficacy for commercial rates of glufosinate, dicamba, quizalofop, and 2,4-D tolerance, (2) agronomic performance, (3) Roundup Hybridization System (RHS) efficacy and glyphosate tolerance, and (4) herbicide pressure testing for tolerance to higher application rates of quizalofop, 2,4-D, glufosinate, and dicamba herbicides was analyzed for all the events tested for constructs HT4-14, HT4-32, and HT4-34. Analysis of the cumulative data demonstrated the overall superior performance of maize event MON87429 compared to the other events and resulted in selection of this event for commercial purposes.

Example 5: Molecular Characterization of Maize Event MON87429

Maize event MON87429 was subjected to extensive molecular characterization upon selection as a commercial event. The transgenic insert of maize event MON87429 contains the elements and sequences described in Table 1.

DNA sequence analysis of maize event MON87429 was conducted. Southern blot analysis was conducted to confirm that plants containing maize event MON87429 contained a single, intact copy of the entire transgenic insert without any transformation vector backbone. Flanking DNA was sequenced on both the 5' and 3' ends of the insert, and the respective junctions were determined using sequence capture, enrichment, sequencing, inverse PCR, and genome walking techniques. The sequences of the flanking DNA for maize event MON87429 were mapped to the known maize genome physical assembly. The insertion site sequence information was used for bioinformatics analysis of the chromosomal location of the event. Insertion site integrity was determined by PCR across the wild-type allele using primers specific to the flanking regions of maize event MON87429. The wild-type insertion site was used to map the unique site of transgene integration for maize event MON87429 to the maize reference genome. To ensure that no alterations or mutations were introduced to any region of the transgene during transformation, the entire transgenic insert of maize event MON87429 was isolated from the plant and sequenced. Sequence information for the 5' junction, 3' junction, and transgenic insert are provided herein as SEQ ID NOs:1-10.

RNA analysis of plants comprising the construct of maize event MON87429 was conducted. Northern analysis was conducted on total RNA isolated from grain of plants containing maize event MON87429. This confirmed the transcript size and number for the pat, dmo, ft_t, and cp4-epsps mRNA products. RNA expression levels for CP4-EPSPS were also measured by real-time PCR using samples from plant tissues containing maize event MON87429. Rapid amplification of cDNA ends (RACE) was used to identify CP4-EPSPS cleavage products to confirm that cleavage of the CP4-EPSPS transcript occurs only in tassels of plants comprising maize event MON87429 and that this is triggered by maize endogenous male-specific small interference RNAs (siRNAs) in a sequence-specific manner. Low molecular weight Northern analysis was performed to demonstrate that there are no CP4-EPSPS siRNAs that could compromise glyphosate tolerance in non-tassel tissues.

Protein analysis of plants comprising the construct of maize event MON87429 was conducted. N-terminal protein sequencing of the expressed PAT, DMO, FT_T, and CP4-EPSPS proteins was performed using immunopurified protein extracts from grain to confirm the authentic N-terminal amino acid sequence. Western blot analysis was conducted on protein extracts from grain containing maize event MON87429 to confirm that a single expected-sized protein was being produced for PAT, DMO, FT_T, and CP4-EPSPS, respectively. ELISAs was used to determine protein levels in the leaf, seed, roots, and pollen of plants for the PAT, DMO, FT_T, and CP4-EPSPS proteins.

Example 6: Detection of Maize Event MON87429

Detection of maize event MON87429 in a sample can be done using DNA, RNA, or protein detection techniques. Exemplary detection methods and materials are provided below. Detection may determine the presence or absence of maize event MON87429 in a sample. Detection may indicate the number of genomic copies of maize event MON87429 (that is, hemizygous, homozygous, or heterozygous) in a sample of genomic DNA.

An event specific endpoint Applied Biosystems™ TAQMAN® thermal amplification method (Thermo Fisher Scientific) was developed to identify maize event MON87429 in a sample. The DNA primers and probe used in the endpoint assay are primers SQ51062 (SEQ ID NO:11), SQ51053 (SEQ ID NO:12), and 6-FAM™ labeled probe PB50370 (SEQ ID NO:13). 6-FAM is a fluorescent dye product of Applied Biosystems (Foster City, Calif.) attached to the DNA probe. For TAQMAN MGB™ probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence. SQ51062 and SQ51053 when used with these reaction methods and PB50370 produce a DNA amplicon that is diagnostic for maize event MON87429. The controls for this analysis should include a positive control containing maize event MON87429, a negative control from non-transgenic maize, and a negative control that contains no template DNA. Additionally, a control for the PCR reaction should optimally include Internal Control Primers and an Internal Control Probe, specific to a single copy gene in the maize genome. These assays are optimized for use with the Applied Biosystems GeneAmp® PCR System 9700 (Thermo Fisher Scientific) run at maximum speed, but other equipment may be used.

An example of conditions useful with TAQMAN methods for detection of maize event MON87429 is as follows. Step 1: 18 megohm water adjusted for final volume of 5 µl. Step 2: 2.28 µl of 2× Universal Master Mix (dNTPs, enzyme, buffer) to a 1× final concentration. Step 3: 0.05 µl Event Primer-1 (SQ51062) and Event Primer-2 (SQ51053) (resuspended in 18 megohm water to a concentration of 100 uM for each primer) to 0.9 µM final concentration. Step 4: 0.01 µl Event 6-FAM MGB Probe PB50370 (resuspended in 18 megohm water to a concentration of 100 µM) to 0.2 µM final concentration. Step 5: 0.05 µl Internal Control Primer-1 and Internal Control Primer-2 Mix (resuspended in 18 megohm water to a concentration of 100 µM for each primer) to 0.9 µM final concentration. Step 6: 0.01 µl Internal Control VIC™ Probe (resuspended in 18 megohm water to a concentration of 100 µM) to 0.2 µM final concentration. Step 7: 2.5 µl Extracted DNA (template) for each sample with one each of the following comprising: (a) Leaf Samples to be analyzed; (b) Negative control (non-transgenic DNA); (c) Negative water control (no template); and (d) Positive control maize containing maize event MON87429 DNA. Step 8: Thermocycler Conditions as follows: one cycle at 95° C. for 20 seconds; forty cycles of 95° C. for 3 seconds then 60° C. for 20 seconds; and final cycle of 10° C.

A zygosity assay is developed to determine whether a plant comprising maize event MON87429 is heterozygous or homozygous for the event or the wild-type allele. An amplification reaction assay can be designed using the sequence information provided herein. For example, such a PCR assay would include design of at least three primers: primer-1, primer-2, and primer-3, where primer-1 is specific to maize genomic DNA on the 3' flank of maize event MON87429; primer-2 is specific to maize event MON87429 transgenic insert; and primer-3 is specific to the wild-type allele. When used as a primer pair in an amplification reaction, primer-1 with primer-2 will produce a PCR amplicon specific for maize event MON87429. When used as a primer pair in an amplification reaction, primer-1 with primer-3 will produce a PCR amplicon specific for wild-type allele. In a PCR reaction performed on maize genomic DNA, the respective PCR amplicons generated from primer-1+primer-2 and that generated from primer-1+primer-3 will differ in sequence and size of the amplicon. When the three primers are included in a PCR reaction with DNA extracted from a plant homozygous for maize event MON87429, only the primer-1+primer-2 amplicon (specific for the maize MON87429 insertion) will be generated. When the three primers are included in a PCR reaction with DNA extracted from a plant heterozygous for maize event MON87429, both the primer-1+primer-2 amplicon (specific for the maize MON87429 insertion) and the primer-1+primer-3 amplicon (specific for wild-type allele or absence of the maize MON87429 insertion) will be generated. When the three primers are mixed together in a PCR reaction with DNA extracted from a plant that is null for maize event MON87429 (that is wild-type), only the primer-1+primer-3 amplicon (specific for wild-type allele) will be generated. The amplicons produced using the PCR reaction may be identified or distinguished using any method known in the art.

Another zygosity assay for maize event MON87429 is a TAQMAN thermal amplification reaction. For this type of assay, in addition to primers as described above, the assay would include two fluorescently labeled probes. Probe-1 would be specific for maize event MON87429, and probe-2 would be specific for a maize plant that is null for maize event MON87429 (wild-type), and where the two probes contain different fluorescent labels, for example the 6-FAM-label or VIC™-label. When used in a TAQMAN reaction, primer-1+primer-2+probe-1 will produce a first fluorescent signal specific for maize event MON87429 and primer-1+primer-3+probe-2 will produce a second fluorescent signal specific for wild-type maize. When the three primers and two probes are included in a TAQMAN reaction with DNA extracted from a plant homozygous for maize event MON87429, only the first fluorescent signal (specific to primer-1+primer-2+probe-1) will be generated. When the three primers are included in a TAQMAN reaction with DNA extracted from a plant heterozygous for maize event MON87429, both the first fluorescent signal (specific to primer-1+primer-2+probe-1) and the second fluorescent signal (specific to primer-1+primer-3+probe-2) will be generated. When the three primers are mixed together in a TAQMAN reaction with DNA extracted from a plant which is null for maize event MON87429 (wild-type), only the second fluorescent signal (specific to primer-1+primer-3+probe-2) will be generated.

Another method to detect the presence of maize event MON87429 in a plant sample would be Southern analysis. One of skill in art would understand how to design Southern hybridization probe(s) specific for maize event MON87429 and a second southern hybridization probe specific for a maize plant which is null for maize event MON87429 (wild-type). With Southern analysis, a signal detected only from the first Southern hybridization probe will be indicative of a plant homozygous for maize event MON87429; a signal detected from both the first Southern hybridization probe and the second Southern hybridization probe will be indicative of a plant heterozygous for maize event MON87429; and a signal detected only from the second Southern hybridization probe will be indicative that the DNA was extracted from a plant that is null for maize event MON87429 (wild-type).

Another example of a detection kit comprises at least one antibody specific for at least one protein encoded by maize event MON87429. For example, such a kit may utilize a lateral flow strip comprising reagents activated when the tip of the strip is contacted with an aqueous solution. Exemplary proteins sufficient for use in antibody production are ones encoded by the sequence provided as SEQ ID NO:10, or any fragment thereof.

A protein detection method is developed to determine whether a sample is from a plant, seed, cell, or plant part comprising maize event MON87429. At least one antibody specific for at least one protein encoded by maize event MON87429 is used to detect a protein encoded by maize event MON87429 in a sample. A detection kit comprising one or more antibodies specific for one or more proteins encoded by maize event MON87429 may utilize a lateral flow strip containing reagents activated when the tip of the strip is contacted with an aqueous solution. Samples of maize tissue may be ground up and protein extracted for analysis using water or an aqueous buffer (e.g., phosphate buffered saline containing detergent and bovine serum albumin). Following centrifugation, the aqueous supernatant is analyzed using the ELISA method in a sandwich format on a lateral flow strip containing an absorbent pad. Detection is activated by dipping the tip of the strip into the aqueous solution containing the sample to be tested. The aqueous solution is carried up the strip by capillary action and solubilizes gold labeled antibodies on the strip. The gold labeled antibodies are specific for at least one protein encoded by maize event MON87429 and will bind to an epitope on the protein in the sample to form an antibody-antigen complex. The gold labeled antibody-antigen complex is then carried up the strip to a nitrocellulose membrane. The membrane comprises a test line of immobilized antibodies that bind to a second, separate epitope on the protein encoded by maize event MON87429, causing a visible line to appear across the test strip if the protein encoded by maize event MON87429 is present in the sample.

What is claimed is:

1. A recombinant DNA molecule comprising a sequence selected from the group consisting of SEQ ID NO:10, SEQ ID NO:9, SEQ ID NO:8, SEQ ID NO:7, SEQ ID NO:6, SEQ ID NO:5, SEQ ID NO:4, SEQ ID NO:3, SEQ ID NO:2, and SEQ ID NO:1.

2. The recombinant DNA molecule of claim 1, wherein
   a) said DNA molecule comprises SEQ ID NO:1 and SEQ ID NO:2; or
   b) said DNA molecule comprises SEQ ID NO:3 and SEQ ID NO:4.

3. The recombinant DNA molecule of claim 1, wherein the recombinant DNA molecule is an amplicon diagnostic for the presence of maize event MON87429.

4. A maize plant, maize seed, maize cell, maize plant part, or maize commodity product comprising a DNA molecule comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10.

5. The maize plant, maize seed, maize cell, or maize plant part of claim 4, wherein the maize plant, maize seed, maize cell, or maize plant part comprises tolerance to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof.

6. The maize plant, maize seed, maize cell, or maize plant part of claim 5, wherein the maize plant, maize seed, maize cell, or maize plant part is tolerant to quizalofop, haloxyfop, dicamba, 2,4-D, glufosinate, and glyphosate.

7. A method for controlling weeds in a crop-growing area comprising:
   a) planting maize comprising maize event MON87429 in the crop-growing area, wherein a representative sample of seed comprising the event have been deposited as ATCC Accession No. PTA-124635; and
   b) applying to the crop-growing area, or any portion thereof, an effective amount of at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof, to control the weeds in the area without injuring the maize.

8. The method of claim 7, wherein applying the effective amount of at least one herbicide comprises applying at least two or more herbicides selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS) over a growing season.

9. The method of claim 7, wherein applying the effective amount of at least one herbicide comprises applying an herbicide selected from the group consisting of quizalofop, haloxyfop, dicamba, 2,4-D, glufosinate, and glyphosate, or any combination thereof.

10. The method of claim 9, wherein the effective amount of dicamba is about 0.5 lb ae/acre to about 2 lb ae/acre of dicamba over a growing season, or wherein the effective amount of glufosinate is about 0.4 lb ai/acre to about 1.59 lb ai/acre over a growing season, or wherein the effective amount of 2,4-D is about 0.75 lb ae/acre to 1.0 lb ae/acre over a growing season, or wherein the effective amount of quizalofop is about 0.034 lb ai/acre to about 0.083 lb ai/acre over a growing season, or wherein the effective amount of haloxyfop is about 0.018 ai/acre to about 0.07 lb ai/acre over a growing season.

11. A method of producing a maize plant that comprises tolerance to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof, the method comprising:
   a) breeding a maize plant comprising maize event MON87429 with itself or a second plant to produce seed, wherein a representative sample of seed comprising the event have been deposited as ATCC Accession No. PTA-124635; and
   b) identifying progeny maize seed that comprise maize event MON87429.

12. The method of claim 11, wherein identifying progeny maize seed that comprise maize event MON87429 comprises:
   a) growing the progeny maize seed to produce progeny maize plants;
   b) treating the progeny maize plants with an effective amount of at least one herbicide selected from the group consisting of quizalofop, haloxyfop, dicamba, 2,4-D, glufosinate, and glyphosate, or any combination thereof; and
   c) selecting a progeny maize plant that is tolerant to at least one herbicide selected from the group consisting of inhibitors of acetyl CoA carboxylase (ACCase) in the aryloxyphenoxy propionate (FOP) group, synthetic auxins, inhibitors of glutamine synthetase, and inhibitors of 5-enolpyruvylshikimate-3-phosphate synthase (EPSPS), or any combination thereof.

13. The method of claim 11, wherein identifying progeny maize seed that comprise maize event MON87429 comprises detecting the presence of maize event MON87429 in a sample derived from the progeny maize seed or wherein identifying progeny maize seed that comprise maize event MON87429 comprises detecting the presence of at least one protein encoded by maize event MON87429 in a sample derived from the progeny maize seed.

14. A method of producing hybrid maize seed comprising:
   a) growing a maize plant comprising SEQ ID NO:10;
   b) applying an effective amount of glyphosate prior to or during the development of the male reproductive tissue of the maize plant thereby inducing male-sterility in the maize plant;
   c) fertilizing the maize plant with pollen from a second maize plant; and
   d) harvesting hybrid maize seed from the maize plant.

15. The method of claim 14, wherein applying the effective amount of glyphosate comprises application of glyphosate prior to or during the development at an effective amount of about 0.5 lb ae/acre to about 2.5 lb ae/acre.

16. The method of claim 14, wherein applying the effective amount of glyphosate comprises applying the glyphosate at a developmental stage selected from the group consisting of the V4, V5, V6, V7, V8, V9, V10, V11, V12, V13, and V14 stage of maize plant development.

17. A hybrid maize seed produced by the method of claim 14, wherein the hybrid maize seed comprises SEQ ID NO:10.

18. A method of determining zygosity of a maize plant for maize event MON87429 comprising:
   a) contacting a sample comprising DNA derived from the maize plant with a primer set capable of producing a first amplicon diagnostic for the presence of maize event MON87429 and a second amplicon diagnostic for the wild-type maize genomic DNA not comprising maize event MON87429;
   b) performing a nucleic acid amplification reaction; and
   c) detecting the first amplicon and the second amplicon, wherein the presence of both amplicons indicates the sample is heterozygous for maize event MON87429 and the presence of only the first amplicon indicates the sample is homozygous for maize event MON87429 wherein a representative sample of seed comprising the event have been deposited as ATCC Accession No. PTA-124635.

19. The method of claim 18, wherein the primer set comprises SEQ ID NO:11 and SEQ ID NO:12.

* * * * *

SEQUENCE LISTING

```
<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 1
ccactcttgt tggtttcat gtccgggaaa                                         30

<210> SEQ ID NO 2
<211> LENGTH: 30
<212> TYPE: DNA
<213> ORGANISM: Artificial Sequence
<220> FEATURE:
<223> OTHER INFORMATION: Chimeric DNA molecule of maize genomic DNA and
``` transgene DNA

<400> SEQUENCE: 2
cggtgcacaa actatagcaa gtgtggtcta                                      30

<210> SEQ ID NO 3
<211> LENGTH: 60
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 3
acttgcaaaa atagaccact cttgtttggt ttcatgtccg ggaaatctac atggatcagc     60

<210> SEQ ID NO 4
<211> LENGTH: 60
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 4
gcacaacaaa cgcaccggtg cacaaactat agcaagtgtg gtctattttt atatagcaag     60

<210> SEQ ID NO 5
<211> LENGTH: 100
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 5
agatactctt gtttggttac acttgcaaaa atagaccact cttgtttggt ttcatgtccg     60
ggaaatctac atggatcagc aatgagtatg atggtcaata                          100

<210> SEQ ID NO 6
<211> LENGTH: 100
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 6
atgacgtccc gcgatcgccc gcacaacaaa cgcaccggtg cacaaactat agcaagtgtg     60
gtctattttt atatagcaag tgaggtcaga taaaataata                          100

<210> SEQ ID NO 7
<211> LENGTH: 1350
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 7
atctacaggg cgcgcagcgg ctgacacatg ggacccacgg gcaaaggcag cggcagactc     60
gcgcgcgaga gcacgcaagc accgattgac gcgcgtgccc cttttgtcgg agaacgaggg    120
tgcgcgatcg tccgtgcatg gttgagacgg ccaggcgggg cccacccatt ggcgccatgc    180

-continued

| | |
|---|---|
| cgcgcgagca gcagctggcc cgcacaggtg caaaggttga gtgggctaga agcgaagacc | 240 |
| tagtccaagc gacggtttct tccttttttc tcttttttc tttttcctt atattttctt | 300 |
| gttttatttt attttcattt tttattttc aaatctaaat ttgaactcaa gtgtgagatt | 360 |
| catactttga attaaatgct cacattcaaa tatcagtagg aatagaatat ttttaactat | 420 |
| atgtttattt tctctatttt atacaatctt ttccttttt cattttaaa cctcaatttg | 480 |
| taaattatat ctaaattcca attttggtca ttagtatact cctactaata tcattttatt | 540 |
| gttatgaaat gcacacacaa taaactccaa cttgatgaat agatatctat ttattctaat | 600 |
| taatttattt gtttggtaga tgttcaaaat atgaaacaca cacatattgt tttctttctt | 660 |
| tttagaaaaa tggtatttt attgtgggac aagaactaaa agtcacctca aaattaaata | 720 |
| ctcatgtata atttgggata tctgaattta ctatttttat ttcttcatat atttaattta | 780 |
| ttattaattt tttttcttat tgggccttac acttatgaga tcatagaggc atgtggatca | 840 |
| gtggcataca agttgaaatt actgccaaaa atgtctgtca tacacaatcc gtgtgtttgg | 900 |
| tttgtggacc agcagagcct ggctactcta atccgtatgt agagaaccaa gctcccacga | 960 |
| gacagactca atgtatccga gatactcttg tttggttaca cttgcaaaaa tagaccactc | 1020 |
| ttgtttggtt tcatgtccgg gaaatctaca tggatcagca atgagtatga tggtcaatat | 1080 |
| ggagaaaaag aaagagtaat taccaattt ttttcaattc aaaaatgtag atgtccgcag | 1140 |
| cgttattata aaatgaaagt acattttgat aaaacgacaa attcgatcc gtcgtattta | 1200 |
| taggcgaaag caataaacaa attattctaa ttcggaaatc tttatttcga cgtgtctaca | 1260 |
| ttcacgtcca aatgggggct tagatgagaa acttcacgat ttggcgcgac taactaagca | 1320 |
| ctagcgtacg ggacccagat atcgaattca | 1350 |

<210> SEQ ID NO 8
<211> LENGTH: 1069
<212> TYPE: DNA
<213> ORGANISM: Artificial Sequence
<220> FEATURE:
<223> OTHER INFORMATION: Chimeric DNA molecule of maize genomic DNA and transgene DNA

<400> SEQUENCE: 8

| | |
|---|---|
| gatcgcccgc acaacaaacg caccggtgca caaactatag caagtgtggt ctatttttat | 60 |
| atagcaagtg aggtcagata aaataataaa taaaatcatt aaattttata tagcaagtgt | 120 |
| ggtctatttt tgcttgtaaa ctacagagaa tatatatatg ttaaatcggt agaacaattg | 180 |
| gctatttaaa ctaaaagatt taaaaaaaac aaagataaaa aatgttttg aactgcgtgt | 240 |
| ctcgagagca gccagcatgc ttccgacctg catgagcagc gatgctcctg gtgaccgcac | 300 |
| gaacggaacc tggcccgatg gatgattttg catcaacagc gcctgtatgc aacgatcatc | 360 |
| caaccaaaca tacttcgctt tgaggatcca cgcctacaac gtccgcgctc gtccatgcaa | 420 |
| ccaaacacac ggaatgtgtt ccatgtgtcc caattgaaag aagtgtattc ggttaacaac | 480 |
| ggaagtcata accgagccag atatagagat agaaccagat ctatcatacc aagaacaccc | 540 |
| ctccaagatt ctagactgca aggaaagatc cactcgtgcg aagacgacca agatgtataa | 600 |
| gatccaatgg agcaaccata cggaagaaga ggctacgtgg gagactgagg attatctatg | 660 |
| caaatactac cccgattgtc tacctaagga agtcagtacg taaccatgcc cagccccct | 720 |
| gccctccgat tccaaatata gaaagatac tcttaatgaa aactgaatta agaaatgaaa | 780 |
| ttaagcgaag aaggacttcc ttctgaagtt gcaaagagga tggcattcga agagcagatt | 840 |

| | |
|---|---|
| tttctcgcga accttaaaaa gctaaccaat actatgcaag caagctataa ccacctcctc | 900 |
| actcctgggt gatctcgact cgaatctcgg ggcgagattc ttttaagggg ggagagctgt | 960 |
| aacacccag gtgttactta gggtttcccc cttagtacct ccatttgtga cctattatca | 1020 |
| catgtggttt ggtttaagaa aaaggcacca aacttgaggg gccaagccc | 1069 |

```
<210> SEQ ID NO 9
<211> LENGTH: 14008
<212> TYPE: DNA
<213> ORGANISM: Artificial Sequence
<220> FEATURE:
<223> OTHER INFORMATION: Transgene insert

<400> SEQUENCE: 9
```

| | |
|---|---|
| ttcatgtccg ggaaatctac atggatcagc aatgagtatg atggtcaata tggagaaaaa | 60 |
| gaaagagtaa ttaccaattt ttttcaatt caaaaatgta gatgtccgca gcgttattat | 120 |
| aaaatgaaag tacattttga taaaacgaca aattacgatc cgtcgtattt ataggcgaaa | 180 |
| gcaataaaca aattattcta attcggaaat ctttatttcg acgtgtctac attcacgtcc | 240 |
| aaatggggc ttagatgaga aacttcacga tttggcgcga ctaactaagc actagcgtac | 300 |
| gggacccaga tatcgaattc aagctgaccg ccaccggcaa acaaccacga atttgtaatg | 360 |
| gtactaggca aattctccgt ttggcggtgt gtgccggcca attacacgtt tttgcggtgt | 420 |
| cctccgacaa aatttgcctt taaaaacaa ttttataaga gaagctccgg agataaaagg | 480 |
| ccgtcaatgt tacaagagtg aagtcgtcta ctccctccat cccaaaaaat gtaattctaa | 540 |
| gtatgagttg tattattatt tttggacaaa aggagtatac cacaagaatg atatcatcgt | 600 |
| catgcttaga tcctttttag taaagcttga gcttctctaa agtagagaa attagaaaaa | 660 |
| aatcacgttt ttgtggtctt gatttctagc ctccacaaaa tctttggttt tacatttttt | 720 |
| gtttgatttt ggtttcagaa gtccttattt atatgtgcta gtttggcagc acttaaaatc | 780 |
| gttagagaga gcctaaacaa aagccttttc aaaacgacct tgagccagat tggttgatgg | 840 |
| ccaaaatttg attgtcaaaa cttaggcaag ccaagatttt agcagctatt tggtttggta | 900 |
| ccaaaatttg ccaatgatct gttcttttgc cttttcaacc ggtttatcag ccgtacttca | 960 |
| gcttattctc tctcacagaa cactattgaa tcagccgaaa agccaccgca gaacaggacc | 1020 |
| agtatctcac aaatggcatg ccaaatatac tcaccgtcag tgagcccgtt taacggcgtc | 1080 |
| gacaagtcta acgccacca accagcgaac caccagcgtc aagctagcca agcgaagcag | 1140 |
| acggccgaga cgttgacacc ttggcgcggg catctctctg gccccctctc gagagttccg | 1200 |
| ctccacctcc actggtggcg gtttccaagt ccgttccgcc tcctgctcct cctcacacgg | 1260 |
| cacgaaaccg tcacggcacc ggcagcacgg gggattcctt tcccaccgct ccttcccttt | 1320 |
| cccttcctcg cccgccgttt taaatagcca gccccatccc cagcttctct ccccaacctc | 1380 |
| agcttctctc gttgttcgga gcgcacacac aacccgatcc ccaatcccct cgtctctcct | 1440 |
| cgcgagcctc gtcgatcccc gcttcaaggt acggcgatca tcctcccttt ctctaccttc | 1500 |
| tcttctctag actaggtcgg cgatccatgg ttagggcctg ctagttctgt tcctgttttt | 1560 |
| ccgtggctgc gaggtacaat agatctgatg gcgttatgat ggttaacttg tcatactcct | 1620 |
| gcggtgtgcg gtctatagtg cttttaggac atcaatttga cctggctcgt tcgagatcgg | 1680 |
| cgatccatgg ttaggaccct aggcggtgga gtcgggttag atccgcgctg tttgtgttag | 1740 |
| tagatggatg cgacctttac ttcagacacg ttctgattgt taacttgtca gcacctggga | 1800 |
| gtcctgggat ggttctagct ggttcgcaga tgagatcgat ttcatgatct gctgtatctt | 1860 |

```
gtttcgttag gttccttttta atctatccgt ggtattatgc taacctatga tatggttcga   1920
tcgtgctagc tacgtcctgt gtcataattt ttagcatgcc cttttttgtt tggttttgtc   1980
tgattgggct gtagatcaga gtatactgtt tcaaactacc tactggatat atttattaaa   2040
tttgaatctg tatgtgtgtc acatatatct tcataattaa aatggatgga aagatatatg   2100
gataggtaca tgtgttgctg tgggttttac tggtactttg ttagatatac atgcttagat   2160
acatgaagca acatgatgtt acagttcaat aattcttgtt tacctaataa acaaataagg   2220
ataggtgtat gttgctgtgg gttttgctgg tactttgtta gatatatatg cttagatata   2280
tgaagcaaca tcctgctacg gtttaataat tattgtttat atctaataga caagcctgct   2340
ttttaattat tttgatatac ttggatgatg gcatacagca gctatgtgtg gattttttaaa   2400
tacccagcat catgagcatg catgaccctg ccttagtatg ctgtttattt gcttgagact   2460
tctttttttg ttggtactca cctttttgtag tttggtgact cttctgcagg tgcaaccatg   2520
tctccggaga ggagaccagt tgagattagg ccagctacag cagctgatat ggccgcggtt   2580
tgtgatatcg ttaaccatta cattgagacg tctacagtga actttaggac agagccacaa   2640
acaccacaag agtggattga tgatctagag aggttgcaag atagataccc ttggttggtt   2700
gctgaggttg agggtgttgt ggctggtatt gcttacgctg ggccctggaa ggctaggaac   2760
gcttacgatt ggacagttga gagtactgtt tacgtgtcac ataggcatca aaggtgggc    2820
ctaggatcca cattgtacac acatttgctt aagtctatgg aggcgcaagg ttttaagtct   2880
gtggttgctg ttataggcct tccaaacgat ccatctgtta ggttgcatga ggctttggga   2940
tacacagccc ggggtacatt gcgcgcagct ggatacaagc atggtggatg gcatgatgtt   3000
ggttttttggc aaagggattt tgagttgcca gctcctccaa ggccagttag gccagttacc   3060
cagatctgat acgcgctgct agtagccaag tacctacctc gagggcacac tgtaggcagt   3120
gtgccatatt acaggttcag attggccggg acaaagagta cactgcgatt ttactatcct   3180
cggtatgctg gtactacagg ttcacattca catggttact acctggcctg tggtatgctg   3240
gtactacagg tgttgctctg aatagctcag gcttgaccca agtaagagca gtgcaaattc   3300
ccaatttcca gaaaacagga ggacctccaa aggacttcaa tgtaattcaa atttctttca   3360
gaggtccttt tgcaagggc tggatgtaaa gtacttttat aataatccaa gccattgtgc    3420
ttctcaaaaa aaggaaaaga aaaaaatttg ttgcggcccg gccgtgacgg ccacgagcga   3480
actcctgcag gagcagactc gcattatcga tggagctcta ccaaactggc cctaggcatt   3540
aacctaccat ggatcacatc gtaaaaaaaa aaccctacca tggatcctat ctgttttctt   3600
tttgccctga aagagtgaag tcatcatcat atttaccatg gcgcgcgtag gagcgcttcg   3660
tcgaagaccc atagggggc ggtactcgca ccgtggttgt ttcctgttat gtaatatcgg    3720
atgggggagc agtcggctag gttggtccca tcggtactgg tcgtcccta gtgcgctaga    3780
tgcgcgatgt ttgtcctcaa aaactctttt cttcttaata acaatcatac gcaaattttt   3840
tgcgtattcg agaaaaaaag aagattctat ctgtttttttt tttgaaatgg ctccaattta   3900
taggaggagc ccgtttaacg gcgtcgacaa atctaacgga caccaaccag cgaatgagcg   3960
aacccaccag cgccaagcta gccaagcgaa gcagacggcc gagacgctga cacccttgcc   4020
ttggcgcggc atctccgtcg ctggctcgct ggctctggcc ccttcgcgag agttccggtc   4080
cacctccacc tgtgtcggtt tccaactccg ttccgccttc gcgtgggact tgttccgttc   4140
atccgttggc ggcatccgga aattgcgtgg cgtagagcac ggggccctcc tctcacacgg   4200
```

```
cacggaaccg tcacgagctc acggcaccgg cagcacggcg gggattcctt ccccaccacc      4260
gctccttccc tttcccttcc tcgcccgcca tcataaatag ccaccctcc cagcttcctt       4320 cgccacatcc tctcatcatc ttctctcgtg tagcacgcgc agcccgatcc ccaatcccct      4380
ctcctcgcga gcctcgtcga tccctcgctt caaggtatgg ctatcgtcct tcctctctct      4440
ctctttacct tatctagatc ggcgatccat ggttagggcc tgctagttct ccgttcgtgt      4500
ttgtcgatgg ctgtgaggca caatagatcc gtcggcgtta tgatggttag cctgtcatgc      4560
tcttgcgatc tgtggttcct ttaggaaagg cattaattta atccctgatg gttcgagatc      4620
ggtgatccat ggttagtacc ctaagctgtg gagtcgggtt tagatccgcg ctgttcgtag      4680
gcgatctgtt ctgattgtta acttgtcagt acctgcgaat cctcggtggt tctagctggt      4740
tcggagatca gatcgattcc attatctgct atacatcttg tttcgttgcc taggctccgt      4800
ttaatctatc catcgtatga tgttagcctt tgatatgatt cgatcgtgct agctatgtcc      4860
tgtggactta attgtcaggt cctaattttt aggaagactg ttccaaacca tctgctggat      4920
ttattaaatt tggatctgga tgtgtcacat acaccttcat aattaaaatg gatgaaaata      4980
tctcttatct tttagatatg gataggcatt tatatgatgc tgtgagtttt actagtactt      5040
tcttagaata tatgtacttt tttagacgga atattgatat gtatacatgt gtagatacat      5100
gaagcaacat gctgctgtag tctaataatt cctgttcatc taataatcaa gtatgtatat      5160
gttctgtgtg ttttattggt atttgattag atatatacat gcttagatac atacatgaag      5220
cagcatgctg ctacagttta atcattattg tttatccaat aaacaaacat gcttttaat       5280 ttatcttgat atgcttggat gacggaatat gcagagattt taagtaccca gcatcatgag      5340
catgcatgac cctgcgttag tatgctgttt atttgcttga gactcttcct tttgtagata      5400
ctcaccctgt tttctggtga tcctactgca ggtgaccggt cgccatggcc accgccacca      5460
ctaccgccac cgctgcgttc tccggcgtgg tgagcgtcgg cactgagacg cgcaggatct      5520
actccttcag ccacctccag ccttctgctg cgttccccgc taagccgtct tcgttcaaga      5580
gcctgaagct gaaacagtcc gcacgcctta cccggcgcct ggaccatagg ccattcgttg      5640
tcaggtgcat gctcaccttc gttaggaacg cctggtacgt cgccgctctc cctgaggagc      5700
tgagcgagaa gcccttgggt cgcaccatcc tagacactcc gttagccctt taccgccagc      5760
ctgacggcgt agtggcggcc ctgcttgaca tctgcccgca taggttcgct ccgctcagcg      5820
acggcatcct cgtcaacggg catcttcagt gcccgtacca cgggctggaa tttgacggcg      5880
gtgggcagtg tgtccacaac ccgcacggca acggcgcacg gccagcttcc ctcaacgtta      5940
ggtcgttccc tgttgtcgag cgcgacgcac tgatctggat ctggcctggc gacccagctc      6000
tggccgatcc aggagccatt cccgacttcg gttgccgcgt ggaccagcc tatcggacgg       6060 tcggcggtta cgggcacgtc gattgtaact ataagctcct tgtggacaac cttatggatt      6120
tgggccacgc tcagtacgtg caccgggcta acgctcagac tgacgccttt gaccgtctcg      6180
aaagggaggt catcgtcggc gacggagaga ttcaggcgct gatgaagatc cctggaggca      6240
cgccctctgt gctcatggcg aagtttctca gaggcgcgaa cacgcccgtg gacgcctgga      6300
acgacatccg ctggaataag gtctccgcga tgctgaactt catcgccgtt gcgcccgagg      6360
gcacacccaa agagcagtca atccacagca gagggaccca tattcttaca ccggaaaccg      6420
aggctagttg ccactacttc ttcggctcgt cacggaattt cgggatagac gatccggaga      6480
tggacggtgt tcttcgatct tggcaagcgc aagctctcgt caaggaagat aaggtggtcg      6540
tggaggctat cgagcgtagg cgcgcctacg ttgaggcgaa cggtattagg cccgcgatgc      6600
```

```
tgtcctgcga cgaggccgca gttagagtgt cgcgcgagat agaaaagctg gagcagctag    6660
aggccgcctg attaattaag gccaaggcga tctatgactg aattgccaat gcaccagcct    6720
gtctacatga tgaataaata aagagtccat ccagtgtgat ggctcatgcc tgtgtgagtg    6780
tgactgaatc catcagtgtg tgtgtgtgtt tgtgtcaacc atgtgtgaat caggtgtcaa    6840
aaatcgtggc tggaaatcca tgtggtttct agctttatgt aaatgttgtt tgtgaaatat    6900
aaatattgtt ttgtgtatgt gaattttact ctctcatttt tctccttgcac tcaccattct    6960 attatagtaa ttttttttaag cggccgctga tgtatccgtc cacggtggtg tgtccaatca    7020
gtgaataatc tagttagtga agccagaagt ccatagtgcc ccttgctctg tcaccatata    7080
tccagttcaa ccgcaccaat ttgccatctc gaactggttc atgttttatt caggttggta    7140
aatgaatttt gccaattcaa tgtagttaga tatttccatg tcattttagt acatttacca    7200
attttttata ttctggctag aaaaggagaa tggtgacgtc tttcggaaga tcaagatcaa    7260
ttatcaagta tcagcaacag cacctgaagg ttggagtgca ttagttgtca ttgagaataa    7320
tgctagctat tcattgcact ggcattagag acagagaggg cgagccagtt tgacatggca    7380
aattagcaca gtcaaactgg atacgtggtg acggagggag gggcactatg aatttttggt    7440
gacggaggga ggggcactat gaattttttgg ctttgctgac gggacacgcc actatggatg    7500
aaattggaca aaatacgaat attcaaggat gaaagtggtc ggtttgatag ttcagggatg    7560
aaatgtgtct ttgggcaaac tttgaggacg aagttgccta ttttgcatta aacgaatata    7620
tttatatacc ccaaaaaaaa gaatacacat ctccactccg agccggcatg tggggtcccc    7680
actagtcagc cactgtatgg cgccgactag ctcaacggcc acgaaccagc caaccaccag    7740
cgcaacctaa acggcgtaaa cgttgacggc atctctctct cgccccgtct cgaagcttcc    7800
gcaccgctcg ctggtcgctg cccggcgccg ctcgtgctgg actctttccg tggcggcttc    7860
cgcgaaattg cgtggtggag aggagagacg gaaccgtcac ggcactggat tccttcccca    7920
cccggcttgg ccggcccctc ctcgcctcca taaataggca ccccgtcctc gcctcctctc    7980
cccacctcat ctcctccttt cccgtgaacc gtgaacacaa cccgacccag atcccctctt    8040
gcgagcttcg tcgatccctc ctccgcgtca aggtacggag cttctcctcc ccttcttct    8100 ctagatcggc gtgttatgtt gtttccgtgg ttgcttggtt ggatgaatcg aatgattctt    8160
agggcctagg aggctggtta gatctgttgc gttctgtttc gtagatggat tttggtgtaa    8220
gatcaggtcg gttccgctgt ttaacttgtg atgctagtgt gattttttggg aggatttgag    8280 ttgttaatct gggagttgtt gggaggttct cgtaggcgga ttgtagatga agtcgcccgc    8340
acgatttgcg tggcttgttg ggtagctagg gttagatctg ctcggatttt tcattgttac    8400
ttattgagag ataatgtagc taaccttac ttgttcatct atgtatctcg tattcgtatt    8460
catctggttc gatggtgcta gatagatgcg cctgatttgt ccgatcgaat gggtagcat    8520 ccgcggcttg tttggtagtg ttctgattga tttgtcgctc tagatctgag tggaataata    8580
ttacatctca acatgttact agaaacttgg tttatagctc cggatttaca tgtttattct    8640
tatgtaaggt tttaaatgaa agatttatgc tactgctgct cgttgatcct ttagcatcca    8700
cctgaggaac atgcatgcat ctgttacttc ttttgatata tgcttagata gttgttagta    8760
tatactgctg ttgttcgatg atccttcagg atgaacatgc atgatcatgt tacttgtttt    8820
tatatgcttc tgctgttcgt tgattcttta gtactaccta cctgatcatc ttgcatgttt    8880
cctgcttgtt agagattaat tgattaggct taccttgttg cctggtgatt cttccttgca    8940
```

```
ggtgggtacc cggaccgatg gcaacagcaa catcagcttc tctgttttca actgtttctt    9000
catcttactc caaagctagc tccataccac attcaagact ccaatctgtg aaattcaact    9060
cagtccctag cttcaccggt ctcaaatcaa cctctctcat ctccggatct gattcctctt    9120
ccttagccaa gactctacgc ggttccgtaa cgaaagcaca aacatctgac aagaagcctt    9180
acggattcaa aatcaacgct atgcacgcgg cgctgactcc tctcaccaac aagtatcgct    9240
ttatcgacgt gcagccgctg acaggcgtcc tcggtgcaga gattacaggc gtggatctgc    9300
gggagcctct cgatgacagc acttggaatg agatcctgga cgcctttcac acctaccaag    9360
tgatctactt tccgggtcaa gctatcacta cgagcagca catcgcgttc tcccgccggt    9420
tcggccctgt ggaccggtg ccgatcttaa agagtatcga gggctatcca gaggtgcaga    9480
tgatacggcg cgaggcgaac gagagcagcc ggttcatcgg agatgactgg cacaccgatt    9540
ccaccttcct ggacgctccg cctgccgccg tggtgatgag agctatcgaa gtgccggagt    9600
atggaggtga cacaggcttc ctctccatgt acagtgcctg ggagacactc tcgcctacga    9660
tgcaagctac catcgaaggc ttaaacgtgg tccactcggc gacgaaggtc ttcgggtcat    9720
tgtaccaggc gactaattgg cgcttctcga acaccagcgt gaaagtgatg gacgtggacg    9780
ccggagatag agagactgtg cacccactcg tcgtgacgca tcctgttacg ggaaggcgcg    9840
cactctactg caaccaggtg tactgccaga gatccaggg aatgacggac gcggagtcga    9900
agtccctgtt gcaattcctt tacgagcacg ccaccaagtt cgacttcacc tgccgggtcc    9960
ggtggaagaa ggaccaagtc ctggtgtggg acaacctgtg taccatgcac cgcgccgtcc   10020
cggactacgc tgggaaattc agatacctga cccgcaccac cgtggcggga gacaagccgt   10080
cgcgttgacg gtccgttaat taatcgagtg tgaaggaagt gaactgagtc tcaagaataa   10140
aaactgcaag tatggcgctc cattccatgg aagacctgca tgcatcctat atatgtgctt   10200
ttatgttcaa gttggagaac tatgtgtgtt gtctttaagt tggagtactc taagctattc   10260
gatctggaga ttatgctgtt tttaataaaa gtttgaagtg tatctgtcct gtttaattag   10320
tttcaagaaa gccaagcgtg tttgggttct aggatgaaca aagtcgtcca agatgcaaga   10380
agttctagag aggtagctac atttctggaa attgttgcat cttcctttct tcaatatata   10440
tatattgtcc tatttcataa tgtcattcta gccagctatc tatattctat atatccattt   10500
ccgttgccat actttattca ctatgttgca tcgagtgagc tgcattgctc tgtactacat   10560
gttacttgat atgtgttgtt cataaacaca cacattaata atgatcagat tgtgaaaaat   10620
acgcgtccga tcctacctgt cacttcatca aaaggacagt agaaaaggaa ggtgcacct   10680
acaaatgcca tcattgcgat aaaggaaagg ctatcattca agatgcctct gccgacagtg   10740
gtcccaaaga tggaccccca cccacgagga gcatcgtgga aaaagaagac gttccaacca   10800
cgtcttcaaa gcaagtggat tgatgtgata cttccactga cgtaagggat gacgcacaat   10860
cccactatcc ttcgcaagac ccttcctcta tataaggaag ttcatttcat ttggagagga   10920
cacgctgaaa tcaccagtct ctctctacaa gatcggggat ctctagccct agaaccatct   10980
tccacacact caagccacac tattggagaa cacacaggga caacacacca taagatccaa   11040
gggaggcctc cgccgccgcc ggtaaccacc ccgcccctct cctctttctt tctccgtttt   11100
tttttccgtc tcggtctcga tctttggcct tggtagtttg ggtgggcgag aggcggcttc   11160
gtgcgcgccc agatcggtgc gcgggagggg cgggatctcg cggctggggc tctcgccggc   11220
gtggatccgg cccggatctc gcggggaatg gggctctcgg atgtagatct gcgatccgcc   11280
gttgttgggg gagatgatgg ggggtttaaa atttccgccg tgctaaacaa gatcaggaag   11340
```

```
aggggaaaag ggcactatgg tttatatttt tatatatttc tgctgcttcg tcaggcttag    11400
atgtgctaga tctttctttc ttcttttgt gggtagaatt tgaatccctc agcattgttc    11460
atcggtagtt tttcttttca tgatttgtga caaatgcagc ctcgtgcgga gctttttgt    11520 aggtagaagt gatcaaccat ggcgcaagtt agcagaatct gcaatggtgt gcagaaccca    11580
tctcttatct ccaatctctc gaaatccagt caacgcaaat ctcccttatc ggtttctctg    11640
aagacgcagc agcatccacg agcttatccg atttcgtcgt cgtggggatt gaagaagagt    11700
gggatgacgt taattggctc tgagcttcgt cctcttaagg tcatgtcttc tgtttccacg    11760
gcgtgcatgc ttcatggagc ttcatctagg ccagctactg ccaggaagtc tagcgggctc    11820
agtggcaccg tgcgcatccc tggcgataaa agtatttcac acaggagctt catgttcgga    11880
ggacttgcta gtggagagac gagaatcact ggtttgcttg agggcgaaga tgttatcaac    11940
accggtaagg cgatgcaagc aatgggtgcc agaatccgaa aagagggcga tacgtggatc    12000
atcgacggtg ttggtaacgg aggattgctc gctcccgaag cgccacttga ctttgggaac    12060
gcagctacgg ggtgccgtct tactatggga ctggtaggcg tgtatgactt tgactctacc    12120
ttcatcggtg acgcgagcct cactaagaga ccaatgggac gagtgctgaa tcccctgagg    12180
gagatgggtg tccaggtgaa atctgaggat ggtgatcgtc ttccggttac tctgcgaggc    12240
cccaagaccc ccacgccaat cacgtacagg gttccgatgg cgtcagcaca ggtcaagtca    12300
gcggtactcc tggcgggcct caacacacct ggaatcacaa ccgtgattga acccatcatg    12360
actagagacc acacggagaa gatgttgcag ggtttcggcg ctaatctaac ggtcgaaacc    12420
gacgccgacg gcgtgaggac aatccgcttg gagggcagag gtaaactgac tggccaagtc    12480
atcgatgtgc ctggagatcc ctcgtccaca gcgtttcccc tcgtagctgc gttgctcgtc    12540
cctggatctg atgtgacgat cctgaatgtc ctcatgaatc caactagaac cggcctcatc    12600
ctcacattgc aggagatggg tgctgacatc gaggttatca atcctaggtt ggcaggtgga    12660
gaggatgtgg ccgatctgcg cgtgcgttct agtacactca aaggcgtgac cgtccctgag    12720
gatcgcgctc catccatgat cgacgagtac cccattctcg ccgttgctgc tgcgtttgcc    12780
gagggcgcaa ctgtaatgaa cggccttgag gagttgaggg ttaaggagag tgacaggctg    12840
tccgcggtgg cgaatggcct gaagctaaac ggcgtggact gcgacgaagg tgaaacgtcc    12900
cttgtagtcc gtggtcgccc agacgggaag ggggttgggga atgcttcggg agctgctgtg    12960
gcgacgcacc ttgatcatag aatcgccatg tcatttctgg tgatgggact tgtctccgag    13020
aatccggtga ccgttgacga tgctaccatg atcgccacct cctttcctga gttcatggac    13080
ctcatggcag gcttggggc caagatcgag ctgtctgata ctaaggccgc ttgacacgtg    13140
agacgacgac cgtgcatggt gatgaatcac agacgacgaa cacgcatgtc gcatcgccgt    13200
cctctttgta tcacacagca tcaccttctt cgctctacta ctcccccgag caatcaccga    13260
ccaataacac caaccatcaa cctcccccgt cgccgccgcc ttcaccgtcc tccctcaca    13320 ccatagaact gcaaatgtcc gcctgcaggg tggggcccat cgtggccagt tatccttagc    13380
tatccgtgtc agaatcatct tatcatcgag tcgagtcgtt atcgtgtcca gtggctctct    13440
cgagtcgaga agccctctat ccatccatcc agtgttaggg gttcttcgtc cgtgatgtta    13500
ccatgaattg agttcgcttt ggttatggtg tttgaactgc ttgttgctat ctatcggaat    13560
gaaatgaaat agaagacaag gagaaaaaaa agagttcgaa agttttgttc gcataccata    13620
tatttccttc cggtgcgcgc tgtttattcc tcgctcagca gcaagattgt ttgatcgata    13680
```

```
ttgcagcaag caattacaca ataaatatat tgctacactg gtacttcaaa ctacactggt   13740
ggtcggtgat tttcaatagc atgaaccttg attgaacatc tgtgtagctt acatctcctt   13800
cgaaagctgc aatgcttgag aacttggaaa gaaattcttg tgatggcaga agctattcac   13860
tgtccttcgc tgcatttaca gtccatacag acacagcatt tccatttgc acaagataga   13920 gaacaacaat cagcctttta ggtcaatccc aagtgtgcat gacgtcccgc gatcgcccgc   13980
acaacaaacg caccggtgca caaactat                                     14008

<210> SEQ ID NO 10
<211> LENGTH: 16068
<212> TYPE: DNA
<213> ORGANISM: Artificial Sequence
<220> FEATURE:
<223> OTHER INFORMATION: Chimeric DNA molecule of maize genomic DNA and
      transgene DNA

<400> SEQUENCE: 10
atctacaggg cgcgcagcgg ctgacacatg ggacccacgg gcaaaggcag cggcagactc     60
gcgcgcgaga gcacgcaagc accgattgac gcgcgtgccc cttttgtcgg agaacgaggg    120
tgcgcgatcg tccgtgcatg gttgagacgg ccaggcgggg cccacccatt ggcgccatgc    180
cgcgcgagca gcagctggcc cgcacaggtg caaaggttga gtgggctaga agcgaagacc    240
tagtccaagc gacggtttct tccttttttc tcttttttc tttttccttt atattttctt    300
gttttatttt atttcatttt tttattttc aaatctaaat ttgaactcaa gtgtgagatt    360
catactttga attaaatgct cacattcaaa tatcagtagg aatagaatat ttttaactat    420
atgtttattt tctctatttt atacaatctt ttcctttttt catttttaaa cctcaatttg    480
taaattatat ctaaattcca attttggtca ttagtatact cctactaata tcatttatt    540 gttatgaaat gcacacacaa taaactccaa cttgatgaat agatatctat ttattctaat    600
taatttattt gtttggtaga tgttcaaaat atgaaacaca cacatattgt tttctttctt    660
tttagaaaaa tggtattttt attgtgggac aagaactaaa agtcacctca aaattaaata    720
ctcatgtata atttgggata tctgaattta ctattttat ttcttcatat atttaattta    780
ttattaattt tttttcttat tgggccttac acttatgaga tcatagaggc atgtggatca    840
gtggcataca agttgaaatt actgccaaaa atgtctgtca tacacaatcc gtgtgtttgg    900
tttgtggacc agcagagcct ggctactcta atccgtatgt agagaaccaa gctcccacga    960
gacagactca atgtatccga gatactcttg tttggttaca cttgcaaaaa tagaccactc   1020
ttgtttggtt tcatgtccgg gaaatctaca tggatcagca atgagtatga tggtcaatat   1080
ggagaaaaag aaagagtaat taccaatttt ttttcaattc aaaaatgtag atgtccgcag   1140
cgttattata aaatgaaagt acattttgat aaaacgacaa attacgatcc gtcgtattta   1200
taggcgaaag caataaacaa attattctaa ttcggaaatc tttatttcga cgtgtctaca   1260
ttcacgtcca aatgggggct tagatgagaa acttcacgat ttggcgcgac taactaagca   1320
ctagcgtacg ggacccagat atcgaattca agctgaccgc caccggcaaa caaccacgaa   1380
tttgtaatgg tactaggcaa attctccgtt tggcggtgtg tgccggccaa ttacacgttt   1440
ttgcggtgtc ctccgacaaa atttgccttt taaaacaat tttataagag aagctccgga   1500
gataaaaggc cgtcaatgtt acaagagtga agtcgtctac tccctccatc ccaaaaaatg   1560
taattctaag tatgagttgt attattattt ttggacaaaa ggagtatacc acaagaatga   1620
tatcatcgtc atgcttagat cctttttagt aaagcttgag cttctctaaa agtagagaaa   1680
```

```
ttagaaaaaa atcacgtttt tgtggtcttg atttctagcc tccacaaaat ctttggtttt    1740
acattttttg tttgattttg gtttcagaag tccttattta tatgtgctag tttggcagca    1800
cttaaaatcg ttagagagag cctaaacaaa agccttttca aaacgacctt gagccagatt    1860
ggttgatggc caaaatttga ttgtcaaaac ttaggcaagc caagatttta gcagctattt    1920
ggtttggtac caaaatttgc caatgatctg ttcttttgcc ttttcaaccg gtttatcagc    1980
cgtacttcag cttattctct ctcacagaac actattgaat cagccgaaaa gccaccgcag    2040
aacaggacca gtatctcaca aatggcatgc caaatatact caccgtcagt gagcccgttt    2100
aacggcgtcg acaagtctaa cggccaccaa ccagcgaacc accagcgtca agctagccaa    2160
gcgaagcaga cggccgagac gttgacacct tggcgcgggc atctctctgg cccctctcg     2220 agagttccgc tccacctcca ctggtggcgg tttccaagtc cgttccgcct cctgctcctc    2280
ctcacacggc acgaaaccgt cacggcaccg gcagcacggg ggattccttt cccaccgctc    2340
cttccctttc ccttcctcgc ccgccgtttt aaatagccag ccccatcccc agcttctctc    2400
cccaacctca gcttctctcg ttgttcggag cgcacacaca cccgatccc caatcccctc     2460 gtctctcctc gcgagcctcg tcgatccccg cttcaaggta cggcgatcat cctcccttc    2520 tctaccttct cttctctaga ctaggtcggc gatccatggt tagggcctgc tagttctgtt    2580 cctgttttc cgtggctgcg aggtacaata gatctgatgg cgttatgatg gttaacttgt     2640
catactcctg cggtgtgcgg tctatagtgc ttttaggaca tcaatttgac ctggctcgtt    2700
cgagatcggc gatccatggt taggaccta ggcggtggag tcgggttaga tccgcgctgt     2760
ttgtgttagt agatggatgc gacctttact tcagacacgt tctgattgtt aacttgtcag    2820
cacctgggag tcctgggatg gttctagctg gttcgcagat gagatcgatt tcatgatctg    2880
ctgtatcttg tttcgttagg ttccttttaa tctatccgtg gtattatgct aacctatgat    2940
atggttcgat cgtgctagct acgtcctgtg tcataatttt tagcatgccc ttttttgttt    3000
ggttttgtct gattgggctg tagatcagag tatactgttt caaactacct actgatata     3060 tttattaaat ttgaatctgt atgtgtgtca catatatctt cataattaaa atggatggaa    3120
agatatatgg ataggtacat gtgttgctgt gggttttact ggtactttgt tagatataca    3180
tgcttagata catgaagcaa catgatgtta cagttcaata attcttgttt acctaataaa    3240
caaataagga taggtgtatg ttgctgtggg ttttgctggt actttgttag atatatatgc    3300
ttagatatat gaagcaacat cctgctacgg tttaataatt attgtttata tctaatagac    3360
aagcctgctt tttaattatt ttgatatact tggatgatgg catacagcag ctatgtgtgg    3420
atttttaaat acccagcatc atgagcatgc atgaccctgc cttagtatgc tgtttatttg    3480
cttgagactt ctttttttgt tggtactcac cttttgtagt ttggtgactc ttctgcaggt    3540
gcaaccatgt ctccggagag gagaccagtt gagattaggc cagctacagc agctgatatg    3600
gccgcggttt gtgatatcgt taaccattac attgagacgt ctacagtgaa ctttaggaca    3660
gagccacaaa caccacaaga gtggattgat gatctagaga ggttgcaaga tagataccct    3720
tggttggttg ctgaggttga gggtgttgtg gctggtattg cttacgctgg gcctggaag     3780 gctaggaacg cttacgattg gacagttgag agtactgttt acgtgtcaca taggcatcaa    3840
aggttgggcc taggatccac attgtacaca catttgctta agtctatgga ggcgcaaggt    3900
tttaagtctg tggttgctgt tataggcctt ccaaacgatc catctgttag gttgcatgag    3960
gctttgggat acacagcccg gggtacattg cgcgcagctg gatacaagca tggtggatgg    4020
catgatgttg gttttggca aagggatttt gagttgccag ctcctccaag gccagttagg    4080
```

```
ccagttaccc agatctgata cgcgctgcta gtagccaagt acctacctcg agggcacact   4140
gtaggcagtg tgccatatta caggttcaga ttggccggga caaagagtac actgcgattt   4200
tactatcctc ggtatgctgg tactacaggt tcacattcac atggttacta cctggcctgt   4260
ggtatgctgg tactacaggt gttgctctga atagctcagg cttgacccaa gtaagagcag   4320
tgcaaattcc caatttccag aaaacaggag gacctccaaa ggacttcaat gtaattcaaa   4380
tttctttcag aggtcctttt gcaaggggct ggatgtaaag tacttttata ataatccaag   4440
ccattgtgct tctcaaaaaa aggaaaagaa aaaatttgt tgcggcccgg ccgtgacggc    4500
cacgagcgaa ctcctgcagg agcagactcg cattatcgat ggagctctac caaactggcc   4560
ctaggcatta acctaccatg gatcacatcg taaaaaaaaa accctaccat ggatcctatc   4620
tgttttcttt ttgccctgaa agagtgaagt catcatcata tttaccatgg cgcgcgtagg   4680
agcgcttcgt cgaagaccca tagggggcg gtactcgcac cgtggttgtt tcctgttatg    4740
taatatcgga tggggagca gtcggctagg ttggtcccat cggtactggt cgtcccctag    4800
tgcgctagat gcgcgatgtt tgtcctcaaa aactcttttc ttcttaataa caatcatacg   4860
caaatttttt gcgtattcga gaaaaaaga agattctatc tgtttttttt ttgaaatggc    4920
tccaatttat aggaggagcc cgtttaacgg cgtcgacaaa tctaacggac accaaccagc   4980
gaatgagcga acccaccagc gccaagctag ccaagcgaag cagacggccg agacgctgac   5040
acccttgcct tggcgcggca tctccgtcgc tggctcgctg gctctggccc cttcgcgaga   5100
gttccggtcc acctccacct gtgtcggttt ccaactccgt tccgccttcg cgtgggactt   5160
gttccgttca tccgttggcg gcatccggaa attgcgtggc gtagagcacg gggccctcct   5220
ctcacacggc acggaaccgt cacgagctca cggcaccggc agcacggcgg ggattccttc   5280
cccaccaccg ctccttccct ttcccttcct cgcccgccat cataaatagc caccctccc    5340
agcttccttc gccacatcct ctcatcatct tctctcgtgt agcacgcgca gcccgatccc   5400
caatcccctc tcctcgcgag cctcgtcgat ccctcgcttc aaggtatggc tatcgtcctt   5460
cctctctctc tctttacctt atctagatcg gcgatccatg gttagggcct gctagttctc   5520
cgttcgtgtt tgtcgatggc tgtgaggcac aatagatccg tcggcgttat gatggttagc   5580
ctgtcatgct cttgcgatct gtggttcctt taggaaaggc attaatttaa tccctgatgg   5640
ttcgagatcg gtgatccatg gttagtaccc taagctgtgg agtcgggttt agatccgcgc   5700
tgttcgtagg cgatctgttc tgattgttaa cttgtcagta cctgcgaatc ctcggtggtt   5760
ctagctggtt cggagatcag atcgattcca ttatctgcta tacatcttgt ttcgttgcct   5820
aggctccgtt taatctatcc atcgtatgat gttagccttt gatatgattc gatcgtgcta   5880
gctatgtcct gtggacttaa ttgtcaggtc ctaatttta ggaagactgt tccaaaccat    5940
ctgctggatt tattaaattt ggatctggat gtgtcacata caccttcata attaaaatgg   6000
atggaaatat ctcttatctt ttagatatgg ataggcattt atatgatgct gtgagttta    6060
ctagtacttt cttagaatat atgtactttt ttagacggaa tattgatatg tatacatgtg   6120
tagatacatg aagcaacatg ctgctgtagt ctaataattc ctgttcatct aataatcaag   6180
tatgtatatg ttctgtgtgt tttattggta tttgattaga tatatacatg cttagataca   6240
tacatgaagc agcatgctgc tacagtttaa tcattattgt ttatccaata aacaaacatg   6300
cttttttaatt tatcttgata tgcttggatg acggaatatg cagagatttt aagtacccag   6360
catcatgagc atgcatgacc ctgcgttagt atgctgttta tttgcttgag actctttctt   6420
```

| | |
|---|---|
| ttgtagatac tcaccctgtt ttctggtgat cctactgcag gtgaccggtc gccatggcca | 6480 |
| ccgccaccac taccgccacc gctgcgttct ccggcgtggt gagcgtcggc actgagacgc | 6540 |
| gcaggatcta ctccttcagc cacctccagc cttctgctgc gttccccgct aagccgtctt | 6600 |
| cgttcaagag cctgaagctg aaacagtccg cacgccttac ccggcgcctg gaccataggc | 6660 |
| cattcgttgt caggtgcatg ctcaccttcg ttaggaacgc ctggtacgtc gccgctctcc | 6720 |
| ctgaggagct gagcgagaag cccttgggtc gcaccatcct agacactccg ttagccctt | 6780 |
| accgccagcc tgacggcgta gtggcggccc tgcttgacat ctgcccgcat aggttcgctc | 6840 |
| cgctcagcga cggcatcctc gtcaacgggc atcttcagtg cccgtaccac gggctggaat | 6900 |
| tgacggcgg tgggcagtgt gtccacaacc cgcacggcaa cggcgcacgg ccagcttccc | 6960 |
| tcaacgttag gtcgttccct gttgtcgagc gcgacgcact gatctggatc tggcctggcg | 7020 |
| acccagctct ggccgatcca ggagccattc ccgacttcgg ttgccgcgtg gacccagcct | 7080 |
| atcggacggt cggcggttac gggcacgtcg attgtaacta taagctcctt gtggacaacc | 7140 |
| ttatggattt gggccacgct cagtacgtgc accgggctaa cgctcagact gacgcctttg | 7200 |
| accgtctcga aagggaggtc atcgtcggcg acggagagat tcaggcgctg atgaagatcc | 7260 |
| ctggaggcac gccctctgtg ctcatggcga gtttctcag aggcgcgaac acgcccgtgg | 7320 |
| acgcctggaa cgacatccgc tggaataagg tctccgcgat gctgaacttc atcgccgttg | 7380 |
| cgcccgaggg cacacccaaa gagcagtcaa tccacagcag agggacccat attcttacac | 7440 |
| cggaaaccga ggctagttgc cactacttct tcggctcgtc acggaatttc gggatagacg | 7500 |
| atccggagat ggacggtgtt cttcgatctt ggcaagcgca agctctcgtc aaggaagata | 7560 |
| aggtggtcgt ggaggctatc gagcgtaggc gcgcctacgt tgaggcgaac ggtattaggc | 7620 |
| ccgcgatgct gtcctgcgac gaggccgcag ttagagtgtc gcgcgagata gaaaagctgg | 7680 |
| agcagctaga ggccgcctga ttaattaagg ccaaggcgat ctatgactga attgccaatg | 7740 |
| caccagcctg tctacatgat gaataaataa agagtccatc cagtgtgatg gctcatgcct | 7800 |
| gtgtgagtgt gactgaatcc atcagtgtgt gtgtgtgttt gtgtcaacca tgtgtgaatc | 7860 |
| aggtgtcaaa atcgtggct ggaaatccat gtggtttcta gctttatgta aatgttgttt | 7920 |
| gtgaaatata aatattgttt tgtgtatgtg aattttactc tctcattttt ctcttgcact | 7980 |
| caccattcta ttatagtaat ttttttaagc ggccgctgat gtatccgtcc acggtggtgt | 8040 |
| gtccaatcag tgaataatct agttagtgaa gccagaagtc catagtgccc cttgctctgt | 8100 |
| caccatatat ccagttcaac cgcaccaatt tgccatctcg aactggttca tgttttattc | 8160 |
| aggttggtaa atgaattttg ccaattcaat gtagttagat atttccatgt cattttagta | 8220 |
| catttaccaa ttttttatat tctggctaga aaaggagaat ggtgacgtct ttcggaagat | 8280 |
| caagatcaat tatcaagtat cagcaacagc acctgaaggt tggagtgcat tagttgtcat | 8340 |
| tgagaataat gctagctatt cattgcactg gcattagaga cagagagggc gagccagttt | 8400 |
| gacatggcaa attagcacag tcaaactgga tacgtggtga cggagggagg ggcactatga | 8460 |
| atttttggtg acggagggag gggcactatg aattttggc tttgctgacg ggacacgcca | 8520 |
| ctatggatga aattggacaa aatacgaata ttcaaggatg aaagtggtcg gtttgatagt | 8580 |
| tcagggatga aatgtgtctt tgggcaaact ttgaggacga agttgcctat tttgcattaa | 8640 |
| acgaatatat ttatataccc caaaaaaaag aatacacatc tccactccga gccggcatgt | 8700 |
| ggggtcccca ctagtcagcc actgtatggc gccgactagc tcaacggcca cgaaccagcc | 8760 |
| aaccaccagc gcaacctaaa cggcgtaaac gttgacggca tctctctctc gccccgtctc | 8820 |

```
gaagcttccg caccgctcgc tggtcgctgc ccggcgccgc tcgtgctgga ctctttccgt  8880
ggcggcttcc gcgaaattgc gtggtggaga ggagagacgg aaccgtcacg gcactggatt  8940
ccttccccac ccggcttggc cggcccctcc tcgcctccat aaataggcac cccgtcctcg  9000
cctcctctcc ccacctcatc tcctcctttc ccgtgaaccg tgaacacaac ccgacccaga  9060
tcccctcttg cgagcttcgt cgatccctcc tccgcgtcaa ggtacggagc ttctcctccc  9120
ccttcttctc tagatcggcg tgttatgttg tttccgtggt tgcttggttg gatgaatcga  9180
atgattctta gggcctagga ggctggttag atctgttgcg ttctgtttcg tagatggatt  9240
ttggtgtaag atcaggtcgg ttccgctgtt taacttgtga tgctagtgtg attttgggga  9300
ggatttgagt tgttaatctg ggagttgttg ggaggttctc gtaggcggat tgtagatgaa  9360
gtcgcccgca cgatttgcgt ggcttgttgg gtagctaggg ttagatctgc tcggattttt  9420
cattgttact tattgagaga taatgtagct aacctttact tgttcatcta tgtatctcgt  9480
attcgtattc atctggttcg atggtgctag atagatgcgc ctgatttgtc cgatcgaatt  9540
gggtagcatc cgcggcttgt ttggtagtgt tctgattgat ttgtcgctct agatctgagt  9600
ggaataatat tacatctcaa catgttacta gaaacttggt ttatagctcc ggatttacat  9660
gtttattctt atgtaaggtt ttaaatgaaa gatttatgct actgctgctc gttgatcctt  9720
tagcatccac ctgaggaaca tgcatgcatc tgttacttct tttgatatat gcttagatag  9780
ttgttagtat atactgctgt tgttcgatga tccttcagga tgaacatgca tgatcatgtt  9840
acttgttttt atatgcttct gctgttcgtt gattctttag tactacctac ctgatcatct  9900
tgcatgtttc ctgcttgtta gagattaatt gattaggctt accttgttgc ctggtgattc  9960
ttccttgcag gtgggtaccc ggaccgatgg caacagcaac atcagcttct ctgtttttcaa 10020
ctgtttcttc atcttactcc aaagctagct ccataccaca ttcaagactc caatctgtga 10080
aattcaactc agtccctagc ttcaccggtc tcaaatcaac ctctctcatc tccggatctg 10140
attcctcttc cttagccaag actctacgcg gttccgtaac gaaagcacaa acatctgaca 10200
agaagcctta cggattcaaa atcaacgcta tgcacgcggc gctgactcct ctcaccaaca 10260
agtatcgctt tatcgacgtg cagccgctga caggcgtcct cggtgcagag attacaggcg 10320
tggatctgcg ggagcctctc gatgacagca cttggaatga gatcctggac gcctttcaca 10380
cctaccaagt gatctacttt ccgggtcaag ctatcactaa cgagcagcac atcgcgttct 10440
cccgccggtt cggccctgtg gacccggtgc cgatcttaaa gagtatcgag ggctatccag 10500
aggtgcagat gatacggcgc gaggcgaacg agagcagccg gttcatcgga gatgactggc 10560
acaccgattc caccttcctg gacgctccgc ctgccgccgt ggtgatgaga gctatcgaag 10620
tgccggagta tggaggtgac acaggcttcc tctccatgta cagtgcctgg gagacactct 10680
cgcctacgat gcaagctacc atcgaaggct taaacgtggt ccactcggcg acgaaggtct 10740
tcgggtcatt gtaccaggcg actaattggc gcttctcgaa caccagcgtg aaagtgatgg 10800
acgtggacgc cggagataga gagactgtgc acccactcgt cgtgacgcat cctgttacgg 10860
gaaggcgcgc actctactgc aaccaggtgt actgccagaa gatccaggga atgacggacg 10920
cggagtcgaa gtccctgttg caattccttt acgagcacgc caccaagttc gacttcacct 10980
gccgggtccg gtggaagaag gaccaagtcc tggtgtggga caacctgtgt accatgcacc 11040
gcgccgtccc ggactacgct gggaaaattca gatacctgac ccgcaccacc gtggcgggag 11100
acaagccgtc gcgttgacgg tccgttaatt aatcgagtgt gaaggaagtg aactgagtct 11160
```

```
caagaataaa aactgcaagt atggcgctcc attccatgga agacctgcat gcatcctata    11220
tatgtgcttt tatgttcaag ttggagaact atgtgtgttg tctttaagtt ggagtactct    11280
aagctattcg atctggagat tatgctgttt ttaataaaag tttgaagtgt atctgtcctg    11340
tttaattagt ttcaagaaag ccaagcgtgt tgggttcta ggatgaacaa agtcgtccaa     11400
gatgcaagaa gttctagaga ggtagctaca tttctggaaa ttgttgcatc ttcctttctt    11460
caatatatat atattgtcct atttcataat gtcattctag ccagctatct atattctata    11520
tatccatttc cgttgccata ctttattcac tatgttgcat cgagtgagct gcattgctct    11580
gtactacatg ttacttgata tgtgttgttc ataaacacac acattaataa tgatcagatt    11640
gtgaaaaata cgcgtccgat cctacctgtc acttcatcaa aaggacagta gaaaaggaag    11700
gtggcaccta caaatgccat cattgcgata aggaaaggc tatcattcaa gatgcctctg     11760
ccgacagtgg tcccaaagat ggacccccac ccacgaggag catcgtggaa aaagaagacg    11820
ttccaaccac gtcttcaaag caagtggatt gatgtgatac ttccactgac gtaagggatg    11880
acgcacaatc ccactatcct tcgcaagacc cttcctctat ataaggaagt tcatttcatt    11940
tggagaggac acgctgaaat caccagtctc tctctacaag atcggggatc tctagcccta    12000
gaaccatctt ccacacactc aagccacact attggagaac acacagggac aacacaccat    12060
aagatccaag ggaggcctcc gccgccgccg gtaaccaccc cgcccctctc ctctttcttt    12120
ctccgttttt ttttccgtct cggtctcgat cttttggcct tggtagtttgg gtgggcgaga    12180 ggcggcttcg tgcgcgccca gatcggtgcg cgggaggggc gggatctcgc ggctggggct    12240
ctcgccggcg tggatccggc ccggatctcg cggggaatgg ggctctcgga tgtagatctg    12300
cgatccgccg ttgttggggg agatgatggg gggtttaaaa tttccgccgt gctaaacaag    12360
atcaggaaga ggggaaaagg gcactatggt ttatattttt atatatttct gctgcttcgt    12420
caggcttaga tgtgctagat cttttctttct ctttttgtg ggtagaattt gaatccctca    12480
gcattgttca tcgtagtttt ttcttttcat gatttgtgac aaatgcagcc tcgtgcggag    12540 ctttttttgta ggtagaagtg atcaaccatg gcgcaagtta gcagaatctg caatggtgtg    12600
cagaacccat ctcttatctc caatctctcg aaatccagtc aacgcaaatc tcccttatcg    12660
gtttctctga agacgcagca gcatccacga gcttatccga tttcgtcgtc gtggggattg    12720
aagaagagtg ggatgacgtt aattggctct gagcttcgtc ctcttaaggt catgtcttct    12780
gtttccacgg cgtgcatgct tcatggagct tcatctaggc cagctactgc caggaagtct    12840
agcgggctca gtggcaccgt gcgcatccct ggcgataaaa gtatttcaca caggagcttc    12900
atgttcggag gacttgctag tggagagacg agaatcactg gtttgcttga gggcgaagat    12960
gttatcaaca ccggtaaggc gatgcaagca atgggtgcca gaatccgaaa agagggcgat    13020
acgtggatca tcgacggtgt tggtaacgga ggattgctcg ctcccgaagc gccacttgac    13080
tttgggaacg cagctacggg gtgccgtctt actatgggac tggtaggcgt gtatgacttt    13140
gactctacct tcatcggtga cgcgagcctc actaagagac caatgggacg agtgctgaat    13200
cccctgaggg agatgggtgt ccaggtgaaa tctgaggatg gtgatcgtct tccggttact    13260
ctgcgaggcc ccaagacccc cacgccaatc acgtacaggg ttccgatggc gtcagcacag    13320
gtcaagtcag cggtactcct ggcgggcctc aacacacctg gaatcacaac cgtgattgaa    13380
cccatcatga ctagagacca cacggagaag atgttgcagg gtttcggcgc taatctaacg    13440
gtcgaaaccg acgccgacgg cgtgaggaca atccgcttgg agggcagagg taaactgact    13500
ggccaagtca tcgatgtgcc tggagatccc tcgtccacag cgtttcccct cgtagctgcg    13560
```

```
ttgctcgtcc ctggatctga tgtgacgatc ctgaatgtcc tcatgaatcc aactagaacc   13620
ggcctcatcc tcacattgca ggagatgggt gctgacatcg aggttatcaa tcctaggttg   13680
gcaggtggag aggatgtggc cgatctgcgc gtgcgttcta gtacactcaa aggcgtgacc   13740
gtccctgagg atcgcgctcc atccatgatc gacgagtacc ccattctcgc cgttgctgct   13800
gcgtttgccg agggcgcaac tgtaatgaac ggccttgagg agttgagggt taaggagagt   13860
gacaggctgt ccgcggtggc gaatggcctg aagctaaacg cgtggactg cgacgaaggt    13920
gaaacgtccc ttgtagtccg tggtcgccca cgcggaagg ggttggggaa tgcttcggga    13980
gctgctgtgg cgacgcacct tgatcataga atcgccatgt catttctggt gatgggactt   14040
gtctccgaga atccggtgac cgttgacgat gctaccatga tcgccacctc ctttcctgag   14100
ttcatggacc tcatggcagg cttggggggcc aagatcgagc tgtctgatac taaggccgct   14160
tgacacgtga gacgacgacc gtgcatggtg atgaatcaca gacgacgaac acgcatgtcg   14220
catcgccgtc ctctttgtat cacacagcat caccttcttc gctctactac tcccccgagc   14280
aatcaccgac caataacacc aaccatcaac ctcccccgtc gccgccgcct tcaccgtcct   14340
cccctcacac catagaactg caaatgtccg cctgcagggt ggggcccatc gtggccagtt   14400
atccttagct atccgtgtca gaatcatctt atcatcgagt cgagtcgtta tcgtgtccag   14460
tggctctctc gagtcgagaa gccctctatc catccatcca gtgttaggtg ttcttcgtcc   14520
gtgatgttac catgaattga gttcgctttg gttatggtgt ttgaactgct tgttgctatc   14580
tatcggaatg aaatgaaata gaagacaagg agaaaaaaaa gagttcgaaa gttttgttcg   14640
cataccatat atttccttcc ggtgcgcgct gtttattcct cgctcagcag caagattgtt   14700
tgatcgatat tgcagcaagc aattacacaa taaatatatt gctacactgg tacttcaaac   14760
tacactggtg gtcggtgatt ttcaatagca tgaaccttaa ttgaacatct gtgtagctta   14820
catctccttc gaaagctgca atgcttgaga acttggaaag aaattcttgt gatggcagaa   14880
gctattcact gtccttcgct gcatttacag tccatacaga cacagcattt ccattttgca   14940
caagatagag aacaacaatc agccttttag gtcaatccca gtgtgcatg acgtcccgcg    15000
atcgcccgca caacaaacgc accggtgcac aaactatagc aagtgtggtc tattttata    15060
tagcaagtga ggtcagataa aataataaat aaaatcatta aattttatat agcaagtgtg   15120
gtctattttt gcttgtaaac tacagagaat atatatatgt taaatcggta gaacaattgg   15180
ctatttaaac taaagatttt aaaaaaaaca aagataaaaa atgttttga actgcgtgtc    15240
tcgagagcag ccagcatgct tccgacctgc atgagcagcg atgctcctgg tgaccgcacg   15300
aacggaacct ggcccgatgg atgattttgc atcaacagcg cctgtatgca acgatcatcc   15360
aaccaaacat acttcgcttt gaggatccac gcctacaacg tccgcgctcg tccatgcaac   15420
caaacacacg gaatgtgttc catgtgtccc aattgaaaga agtgtattcg gttaacaacg   15480
gaagtcataa ccgagccaga tatagagata gaaccagatc tatcatacca agaacacccc   15540
tccaagattc tagactgcaa ggaaagatcc actcgtgcga agacgaccaa gatgtataag   15600
atccaatgga gcaaccatac ggaagaagag gctacgtggg agactgagga ttatctatgc   15660
aaatactacc ccgattgtct acctaaggaa gtcagtacgt aaccatgccc cagcccctg    15720
ccctccgatt ccaaatatag aaaagatact cttaatgaaa actgaattaa gaaatgaaat   15780
taagcgaaga aggacttcct tctgaagttg caaagaggat ggcattcgaa gagcagattt   15840
ttctcgcgaa ccttaaaaag ctaaccaata ctatgcaagc aagctataac cacctcctca   15900
```

```
ctcctgggtg atctcgactc gaatctcggg gcgagattct tttaaggggg gagagctgta    15960 acacccagg tgttacttag ggtttccccc ttagtacctc catttgtgac ctattatcac    16020
atgtggtttg gtttaagaaa aaggcaccaa acttgagggg ccaagccc                16068

<210> SEQ ID NO 11
<211> LENGTH: 29
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 11
ttgctatata aaatagacc acacttgct                                          29

<210> SEQ ID NO 12
<211> LENGTH: 17
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 12
catgacgtcc cgcgatc                                                      17

<210> SEQ ID NO 13
<211> LENGTH: 16
<212> TYPE: DNA
<213> ORGANISM: Artificial Sequence
<220> FEATURE:
<223> OTHER INFORMATION: Chemically Synthesized Oligonucleotide PCR
      Probe

<400> SEQUENCE: 13
cacaacaaac gcaccg                                                       16
```